(12) United States Patent
Bao et al.

(10) Patent No.: US 7,077,865 B2
(45) Date of Patent: *Jul. 18, 2006

(54) METHOD OF MAKING AN INTERVERTEBRAL DISC PROSTHESIS

(75) Inventors: Qi-Bin Bao, Bloomington, MN (US); Robert Garryl Hudgins, Centerville, MN (US); Jeffrey C. Felt, Greenwood, MN (US); Alexander Arsenyev, Eagan, MN (US); Hansen A. Yuan, Fayetteville, NY (US)

(73) Assignee: Disc Dynamics, Inc., Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/365,842

(22) Filed: Feb. 13, 2003

(65) Prior Publication Data

US 2003/0195628 A1 Oct. 16, 2003

Related U.S. Application Data

(60) Continuation-in-part of application No. 09/649,491, filed on Aug. 28, 2000, now abandoned, which is a continuation-in-part of application No. 08/993,468, filed on Dec. 18, 1997, now Pat. No. 6,306,177, which is a continuation of application No. PCT/US97/20874, filed on Nov. 14, 1997, which is a continuation-in-part of application No. 08/903,455, filed on Jul. 30, 1997, now abandoned, and a continuation-in-part of application No. 08/749,429, filed on Nov. 15, 1996, now abandoned, which is a continuation-in-part of application No. 08/742,444, filed on Nov. 2, 1996, now Pat. No. 5,795,353, which is a continuation-in-part of application No. 08/590,293, filed on Jan. 23, 1996, now Pat. No. 5,888,220, which is a continuation of application No. 08/474,113, filed on Jun. 7, 1995, now abandoned, which is a division of application No. 08/239,248, filed on May 6, 1994, now Pat. No. 5,556,429.

(60) Provisional application No. 60/056,624, filed on Aug. 20, 1997.

(51) Int. Cl.
*A61F 2/44* (2006.01)

(52) U.S. Cl. .................. 623/17.12; 623/18.11; 623/66

(58) Field of Classification Search .. 623/17.11–17.16, 623/18.11; 606/61, 90
See application file for complete search history.

(56) References Cited

U.S. PATENT DOCUMENTS

| | | |
|---|---|---|
| 3,030,951 A | 4/1962 | Mandarino |
| 3,223,083 A | 12/1965 | Cobey |
| 3,320,131 A | 5/1967 | Smith |
| 3,805,767 A | 4/1974 | Erb |
| 3,875,595 A | 4/1975 | Froning |
| 3,879,767 A | 4/1975 | Stubstab |
| RE29,345 E | 8/1977 | Erb |
| 4,052,753 A | 10/1977 | Dedo |
| 4,085,466 A | 4/1978 | Goodfellow et al. |
| 4,098,626 A | 7/1978 | Graham et al. |
| 4,203,444 A | 5/1980 | Bonnell et al. |
| 4,245,623 A | 1/1981 | Erb |
| 4,274,414 A | 6/1981 | Johnson et al. |
| 4,292,972 A | 10/1981 | Pawelchak et al. |
| 4,368,040 A | 1/1983 | Weissman |
| 4,385,404 A | 5/1983 | Sully et al. |
| 4,446,578 A | 5/1984 | Perkins et al. |
| 4,456,745 A | 6/1984 | Rajan |
| 4,463,141 A | 7/1984 | Robinson |
| 4,476,293 A | 10/1984 | Robinson |
| 4,477,604 A | 10/1984 | Oechsle, III |
| 4,570,270 A | 2/1986 | Oechsle, III |
| 4,594,380 A | 6/1986 | Chapin et al. |
| 4,647,643 A | 3/1987 | Zdrahala et al. |
| 4,651,736 A | 3/1987 | Sanders |
| 4,705,038 A | 11/1987 | Sjostrom et al. |
| 4,722,948 A | 2/1988 | Sanderson |
| 4,734,097 A | 3/1988 | Tanabe et al. |
| 4,743,632 A | 5/1988 | Marinovic |
| 4,759,766 A | 7/1988 | Buettner-Janz et al. |

| | | | | | | |
|---|---|---|---|---|---|---|
| 4,772,287 A | 9/1988 | Ray et al. | | 5,591,235 A | 1/1997 | Kuslich |
| 4,808,691 A | 2/1989 | König et al. | | 5,601,590 A | 2/1997 | Bonutti et al. |
| 4,834,729 A | 5/1989 | Sjostrom | | 5,620,649 A | 4/1997 | Trotta |
| 4,834,757 A | 5/1989 | Brantigan | | 5,624,463 A | 4/1997 | Stone et al. |
| 4,842,578 A | 6/1989 | Johnson et al. | | 5,632,275 A | 5/1997 | Browne et al. |
| 4,863,477 A | 9/1989 | Monson | | 5,645,597 A | 7/1997 | Krapiva |
| 4,873,308 A | 10/1989 | Coury et al. | | 5,674,295 A | 10/1997 | Ray et al. |
| 4,880,610 A | 11/1989 | Constantz | | 5,674,296 A | 10/1997 | Bryan et al. |
| 4,904,260 A | 2/1990 | Ray et al. | | 5,769,817 A | 6/1998 | Burgmeier |
| 4,913,701 A | 4/1990 | Tower | | 5,795,353 A | 8/1998 | Felt |
| 4,932,969 A | 6/1990 | Frey et al. | | 5,797,877 A | 8/1998 | Hamilton et al. |
| 4,969,888 A | 11/1990 | Scholten et al. | | 5,800,549 A | 9/1998 | Bao et al. |
| 4,983,179 A | 1/1991 | Sjostrom | | 5,824,093 A | 10/1998 | Ray et al. |
| 5,002,576 A | 3/1991 | Fuhrmann et al. | | 5,827,289 A | 10/1998 | Reiley et al. |
| 5,007,940 A | 4/1991 | Berg | | 5,827,318 A | 10/1998 | Bonutti |
| 5,047,055 A | 9/1991 | Bao et al. | | 5,830,125 A | 11/1998 | Scribner et al. |
| 5,059,193 A | 10/1991 | Kuslich | | 5,834,011 A | 11/1998 | Rose et al. |
| 5,064,426 A | 11/1991 | Huebsch | | 5,860,997 A | 1/1999 | Bonutti |
| 5,067,964 A | 11/1991 | Richmond et al. | | 5,888,220 A | 3/1999 | Felt et al. |
| 5,071,437 A | 12/1991 | Steffee | | 5,895,427 A | 4/1999 | Kuslich et al. |
| 5,078,720 A | 1/1992 | Burton et al. | | 5,895,428 A | 4/1999 | Berry |
| 5,082,803 A | 1/1992 | Sumita | | 5,954,739 A | 9/1999 | Bonutti |
| 5,108,404 A | 4/1992 | Scholten et al. | | 5,972,015 A | 10/1999 | Scribner et al. |
| 5,109,077 A | 4/1992 | Wick | | 5,989,256 A | 11/1999 | Kuslich et al. |
| 5,130,347 A | 7/1992 | Mitra | | 6,001,130 A | 12/1999 | Bryan et al. |
| 5,143,942 A | 9/1992 | Brown | | 6,017,305 A | 1/2000 | Bonutti |
| 5,156,777 A | 10/1992 | Kaye | | 6,019,760 A | 2/2000 | Metz-Stavenhagen et al. |
| 5,163,949 A | 11/1992 | Bonutti | | 6,022,376 A | 2/2000 | Assell et al. |
| 5,166,115 A | 11/1992 | Brown | | 6,048,346 A | 4/2000 | Reiley et al. |
| 5,171,244 A | 12/1992 | Caspari et al. | | 6,053,904 A | 4/2000 | Scribner et al. |
| 5,171,280 A | 12/1992 | Baumgartner | | 6,056,749 A | 5/2000 | Kuslich |
| 5,192,326 A | 3/1993 | Bao et al. | | 6,066,154 A | 5/2000 | Reiley et al. |
| 5,228,459 A | 7/1993 | Caspari et al. | | 6,074,391 A | 6/2000 | Metz-Stavenhagen et al. |
| 5,254,662 A | 10/1993 | Szycher et al. | | 6,086,589 A | 7/2000 | Kuslich et al. |
| 5,258,028 A | 11/1993 | Ersek et al. | | 6,090,110 A | 7/2000 | Metz-Stavenhagen |
| 5,263,498 A | 11/1993 | Caspari et al. | | 6,096,039 A | 8/2000 | Stoltenberg et al. |
| 5,278,201 A | 1/1994 | Dunn | | 6,102,928 A | 8/2000 | Bonutti |
| 5,288,797 A | 2/1994 | Khalil et al. | | 6,106,557 A | 8/2000 | Robioneck et al. |
| 5,290,306 A | 3/1994 | Trotta et al. | | 6,110,210 A | 8/2000 | Norton et al. |
| 5,295,994 A | 3/1994 | Bonutti | | 6,113,639 A | 9/2000 | Ray et al. |
| 5,304,181 A | 4/1994 | Caspari et al. | | 6,127,597 A | 10/2000 | Beyar et al. |
| 5,314,477 A | 5/1994 | Marnay | | 6,132,465 A | 10/2000 | Ray et al. |
| 5,314,478 A | 5/1994 | Oka et al. | | 6,139,550 A | 10/2000 | Michelson |
| 5,320,611 A | 6/1994 | Bonutti et al. | | 6,139,551 A | 10/2000 | Michelson et al. |
| 5,331,975 A | 7/1994 | Bonutti | | 6,140,452 A | 10/2000 | Felt et al. |
| 5,334,201 A | 8/1994 | Cowan | | 6,149,686 A | 11/2000 | Kuslich et al. |
| 5,342,305 A | 8/1994 | Shonk | | RE37,005 E | 12/2000 | Michelson et al. |
| 5,344,444 A | 9/1994 | Glastra | | 6,156,067 A | 12/2000 | Bryan et al. |
| 5,344,456 A | 9/1994 | Nonami et al. | | 6,171,236 B1 | 1/2001 | Bonutti |
| 5,344,459 A | 9/1994 | Swartz | | 6,171,299 B1 | 1/2001 | Bonutti |
| 5,376,064 A | 12/1994 | Cerny | | 6,183,518 B1 | 2/2001 | Ross et al. |
| 5,385,469 A | 1/1995 | Weissman | | 6,187,023 B1 | 2/2001 | Bonutti |
| 5,395,376 A | 3/1995 | Caspari et al. | | 6,187,048 B1 | 2/2001 | Milner et al. |
| 5,411,477 A | 5/1995 | Saab | | 6,193,721 B1 | 2/2001 | Michelson |
| 5,425,772 A | 6/1995 | Brantigan | | 6,193,755 B1 | 2/2001 | Metz-Stavenhagen et al. |
| 5,447,497 A | 9/1995 | Sogard et al. | | 6,214,006 B1 | 4/2001 | Metz-Stavenhagen |
| 5,458,638 A | 10/1995 | Kuslich et al. | | RE37,161 E | 5/2001 | Michelson et al. |
| 5,458,642 A | 10/1995 | Beer et al. | | 6,224,630 B1 | 5/2001 | Bao et al. |
| 5,458,643 A | 10/1995 | Oka et al. | | 6,235,043 B1 | 5/2001 | Reiley et al. |
| 5,470,314 A | 11/1995 | Walinsky | | 6,241,734 B1 | 6/2001 | Scribner et al. |
| 5,489,308 A | 2/1996 | Kuslich et al. | | 6,241,770 B1 | 6/2001 | Michelson |
| 5,514,153 A | 5/1996 | Bonutti | | 6,245,107 B1 | 6/2001 | Ferree |
| 5,529,653 A | 6/1996 | Glastra | | 6,248,110 B1 | 6/2001 | Reiley et al. |
| 5,534,028 A | 7/1996 | Bao et al. | | 6,248,131 B1 | 6/2001 | Felt et al. |
| 5,545,229 A | 8/1996 | Parsons et al. | | 6,264,695 B1 | 7/2001 | Stoy |
| 5,549,679 A | 8/1996 | Kuslich | | 6,277,136 B1 | 8/2001 | Bonutti |
| 5,556,429 A | 9/1996 | Felt | | 6,280,456 B1 | 8/2001 | Scribner et al. |
| 5,562,736 A | 10/1996 | Ray et al. | | 6,280,475 B1 | 8/2001 | Bao et al. |
| 5,571,189 A | 11/1996 | Kuslich | | 6,287,343 B1 | 9/2001 | Kuslich et al. |
| 5,573,517 A | 11/1996 | Bonutti et al. | | 6,306,170 B1 | 10/2001 | Ray |
| 5,587,125 A | 12/1996 | Roychowdhury | | 6,306,177 B1 | 10/2001 | Felt et al. |
| 5,589,563 A | 12/1996 | Ward et al. | | RE37,479 E | 12/2001 | Kuslich |
| 5,591,199 A | 1/1997 | Porter et al. | | 6,350,283 B1 | 2/2002 | Michelson |

| | | | |
|---|---|---|---|
| 6,358,266 B1 | 3/2002 | Bonutti | |
| 6,364,880 B1 | 4/2002 | Michelson | |
| 6,371,990 B1 | 4/2002 | Feree | |
| 6,391,058 B1 | 5/2002 | Kuslich et al. | |
| 6,395,034 B1 | 5/2002 | Suddaby | |
| 6,425,919 B1 | 7/2002 | Lambrecht | |
| 6,428,576 B1 | 8/2002 | Haldimann | |
| 6,443,988 B1 | 9/2002 | Felt et al. | |
| 6,458,889 B1 | 10/2002 | Trollsas et al. | |
| 6,482,235 B1 | 11/2002 | Lambrecht et al. | |
| 6,508,839 B1 | 1/2003 | Lambrecht et al. | |
| 6,534,591 B1 | 3/2003 | Rhee et al. | |
| 6,558,390 B1 | 5/2003 | Cragg | |
| 6,592,625 B1 | 7/2003 | Cauthen | |
| 6,613,054 B1 | 9/2003 | Scribner et al. | |
| 6,623,505 B1 | 9/2003 | Scribner et al. | |
| 2001/0011174 A1 | 8/2001 | Reiley et al. | |
| 2001/0034553 A1 | 10/2001 | Michelson | |
| 2001/0041896 A1 | 11/2001 | Reiley et al. | |
| 2001/0047207 A1 | 11/2001 | Michelson | |
| 2001/0047208 A1 | 11/2001 | Michelson | |
| 2002/0004683 A1 | 1/2002 | Michelson | |
| 2002/0010511 A1 | 1/2002 | Michelson | |
| 2002/0013624 A1 | 1/2002 | Michelson | |
| 2002/0016583 A1 | 2/2002 | Cragg | |
| 2002/0016595 A1 | 2/2002 | Michelson | |
| 2002/0022843 A1 | 2/2002 | Michelson | |
| 2002/0026195 A1 | 2/2002 | Layne et al. | |
| 2003/0033017 A1 | 2/2003 | Lotz et al. | |
| 2003/0069641 A1 | 4/2003 | Reuter et al. | |

FOREIGN PATENT DOCUMENTS

| | | | |
|---|---|---|---|
| EP | 0 353 936 | | 2/1990 |
| EP | 0 505 634 | | 9/1992 |
| EP | 0 521 573 | | 1/1993 |
| FR | 2 639 823 | | 6/1990 |
| WO | WO 93/11723 | | 6/1993 |
| WO | WO 95/30388 | | 11/1995 |
| WO | WO 95/31946 | * | 11/1995 |
| WO | WO 95/31948 | | 11/1995 |
| WO | WO 97/26847 | | 7/1997 |
| WO | WO 98/20939 | | 5/1998 |
| WO | WO 99/44509 | | 9/1999 |
| WO | WO 99/56800 | | 11/1999 |
| WO | WO 99/61084 | | 12/1999 |
| WO | WO 00/02613 | | 1/2000 |
| WO | WO 00/04851 | | 2/2000 |
| WO | WO 00/13619 | | 3/2000 |
| WO | WO 00/13620 | | 3/2000 |
| WO | WO 00/59412 | | 10/2000 |
| WO | WO 00/61037 | | 10/2000 |
| WO | WO 00/64385 | | 11/2000 |
| WO | WO 00/66044 | | 11/2000 |
| WO | WO 00/69374 | | 11/2000 |
| WO | WO 00/74606 | | 12/2000 |
| WO | WO 01/10316 A1 | | 2/2001 |
| WO | WO 01/12107 A1 | | 2/2001 |
| WO | WO 01/60234 A2 | | 8/2001 |
| WO | WO 01/60270 A1 | | 8/2001 |
| WO | WO 01/89428 A2 | | 11/2001 |
| WO | WO 01/93784 A2 | | 12/2001 |
| WO | WO 01/95837 A1 | | 12/2001 |
| WO | WO 02/13731 A1 | | 2/2002 |
| WO | WO 02/17824 A2 | | 3/2002 |
| WO | WO 02/17825 | | 3/2002 |
| WO | WO 02/17825 A2 | | 3/2002 |

OTHER PUBLICATIONS

A. Takahara, et al., "Effect of Soft Segment Chemistry on the Biostability of Segmented Polyurethanes. I. In vitro Oxidation", J. Biomedical Materials Research, 25:341-356 (1991).

A. Takahara, et al., "Effect of Soft Segment Chemistry on the Biostability of Segmented Polyurethanes. II. In vitro Hydrolytic Degradation and Lipid Sorption", J. Biomedical Materials Research, 26:801-818 (1992).

Peppas et al. "New Challenges in Biomaterials", Science, 263:1715-1720 (1994).

Frederick H. Silver, ed., Chapter 1, in *Biomaterials, Medical Devices and Tissue Engineering: An Integrated Approach*, Chapman and Hall, 1994.

Hergenrother et al., "Effect of hard segment chemistry and strain on the stability of polyurethanes: in vivo biostability", Biomaterials, 14:449-458 (1993).

Hill West, et al., "Prevention of Postoperative Adhesions in the Rat by In Situ Photopolymerization of Bioresorbable Hydrogel Barriers," Obstet. Gynecol. 83(1):59-64 (1994).

Brauer and Antonucci, "Dental Applications" *Concise Encyclopedia of Polymer Science and Engineering*, pp. 257-258.

J. Brydson, ed., "Polyurethanes and Polyisocanurates", Chapter 27 in *Plastics Materials*, 6th ed. Butterworth Heeinemann (1995).

"Silicones", pp. 1048-1059 in *Concise Encyclopedia of Polymer Science and Engineering*, Eds. Mark et al., Wiley and Sons, 1990.

"Hydrogels", pp. 458-459 in *Concise Encyclopedia of Polymer Science and Engineering*, Eds. Mark et al., Wiley and Sons, 1990.

Constantz, Brent R., et al., "Skeletal Repair by in Situ Formation of the Mineral Phase of Bone," *Science*, vol. 267, Mar. 24, 1995, pp. 1796-1799.

Alf L. Nachemson, "Challenge of the Artifical Disc", *Clinical Efficacy and Outcome in the Diagnosis and Treatment of Low Back Pain*, edited by J.N. Weinstein, Raven Press, Ltd., NY (1992).

R. Roy-Camille et al., "Experimental Study of Lumbar Disc Replacement", from S.O.F.C.O.T. Annual Meeting, Nov. 1977 Suppl. II. Rev. Chir. orthop. 64, (1978) (uncertified translation).

Buttner-Janz, K. et al., "Orthopedics and Traumatology", *Intervertebral Disk Prosthetics. Development and Current Status.*, Beitr. Orthop. Traumatol., vol. 37, (Mar. 1990), No. 3, pp. 137-147.

M. Szycher, "Biostability of polyurethane elastomers: a critical review", J. Biomater. Appl., 3(2):297-402 (1988).

A. Coury, et al., "Factors and interactions affecting the performance of polyurethane elastomers in medical devices", J. Biomater. Appl. 3(2):130-179 (1988).

Pavlova M, et al., Biocompatible and biodgradable polyurethane polymers:, Biomaterials 14(13):1024-1029 (1993).

Kroschwitz, ed., "Casting", pp. 109-110 in *Concise Encyclopedia of Polymer Science and Engineering*, John Wiley & Sons (1990).

Bao et al., "The artifical disc—theory, design and materials", Biomaterials 17:1157-1167 (1996).

Osti et al., Annular Tears and Disc Degeneration in the Lubmbar Spine, *J. Bone and Joint Surgery*, 74-B(5), pp. 678-682 (1982).

Osti et al., Annulus Tears and Intervertebral Disc Degeneration, *Spine*, 15(8) pp. 762-767 (1990).

Kamblin et al., Development of Degenerative Spondylosis of the Lumbar Spine after Partial Discectomy, *Spine*, 20(5) pp. 599-607, (1995).

Adamus, Dan "Polycarbonate Inflation Devices Simplify Balloon Angioplasty".

DeLong, W.B., "Microsurgical Disectomy and Spinal Decompression", 75:1029-1045.

Erb, R., et al., Hysteroscopic Oviductal Blocking with Formed-in-Place Silicone Rubber Plugs, *Journal of Reproductive Medicine*, 23:65-68 (1979).

Garcia, A., "Intradiscal Polymerization: Preliminary Results of Chemical and Biomechanical Studies", *The Artificial Disc* (1991).

Kambin, P., "Arthrosopic Microdiscectomy: Lumbar and Thoracic", 73 1002-1015.

T.P. Reed et al., "Tubal Occlusion with Silicone Rubber", *Journal of Reproductive Medicine*, vol. 25, No. 1, Jul. 1980, pp. 25-28.

Regan, J., et al., "Atlas of Endoscopic Spine Surgery", pp. 338-345.

Simmons, J. et al., "Posterior Lumbar Interbody Fusion: Biomechanical Selection for Fusions", 81:1100-1111 (1995).

"Guide to Medical Plastics", pp. 41-78 in *Medical Device & Diagnostic Industry*, Apr. 1994.

* cited by examiner

*Primary Examiner*—Bruce Snow
(74) *Attorney, Agent, or Firm*—Faegre & Benson LLP

(57) ABSTRACT

A system for repairing an intervertebral disc by delivering and curing a biomaterial in situ within the disc. The system includes both a device, having an insertable balloon and related lumen, controls and adapters, as well as an in situ curable biomaterial (and related biomaterial delivery means). The system can allow the doctor to determine a suitable endpoint for biomaterial delivery, by controlling distraction and/or biomaterial delivery pressure, and in turn, to deliver a desired quantity of biomaterial to the balloon in order to achieve improved polymer cure and implant characteristics. Also provided is a related method for repairing an intervertebral disc by using such a system to deliver and cure the biomaterial in situ. The system can be used to implant a prosthetic total disc, or a prosthetic disc nucleus in a manner that leaves the surrounding disc tissue substantially intact.

72 Claims, 13 Drawing Sheets

METHOD OF MAKING AN INTERVERTEBRAL DISC PROSTHESIS

CROSS REFERENCE TO RELATED APPLICATION

This application is a continuation-in-part of Ser. No. 09/649,491, filed Aug. 28, 2000, now abandoned, for INTERVERTEBRAL DISC PROSTHESIS, which is a continuation-in-part of Ser. No. 08/993,468, now U.S. Pat. No. 6,306,177, filed Dec. 18, 1997 for BIOMATERIAL SYSTEM FOR IN SITU TISSUE REPAIR, which is a continuation application of International Patent Application Serial No. PCT/US97/20874, filed Nov. 14,1997 for BIOMATERIAL SYSTEM FOR INSITU TISSUE REPAIR; and said Ser. No. 08/993,468 claims priority to U.S. provisional application Ser. No. 60/056,624, filed Aug. 20, 1997 for JOINT RESURFACING SYSTEM; and as a continuation-in-part of U.S. patent application Ser. No. 08/749,429, filed Nov. 15, 1996, now abandoned, for MINIMALLY INVASIVE RESURFACING SYSTEM, which is a continuation-in-part of application Ser. No. 08/742,444, filed on Nov. 2, 1996, issued Aug. 18, 1998 as U.S. Pat. No. 5,795,353, for JOINT RESURFACING SYSTEM, which is a continuation of application Ser. No. 08/474,113 filed on Jun. 7, 1995, now abandoned, which is a divisional of prior application Ser. No. 08/239,248, filed on May 6, 1994, now U.S. Pat. No. 5,556,429, issued Sep. 17, 1996, for JOINT RESURFACING SYSTEM; and said Ser. No. 08/993,468 is a continuation-in-part of U.S. patent application Ser. No. 08/903,455, filed Jul. 30, 1997, now abandoned, which is a continuation-in-part of application Ser. No. 08/590,293, filed Jan. 23, 1996, issued Mar. 30, 1999 as U.S. Pat. No. 5,888,220 for ARTICULATING JOINT REPAIR.

FIELD OF THE INVENTION

The invention disclosed herein relates to the field of orthopedic methods and devices. In particular, the invention relates to field of implantable prostheses, and more particularly, to methods and devices for repair of intervertebral discs.

BACKGROUND OF THE INVENTION

The intervertebral discs, which are located between adjacent vertebrae in the spine, provide structural support for the spine as well as the distribution of forces exerted on the spinal column. An intervertebral disc consists of three major components: cartilage endplates, nucleus pulpous, and annulus fibrosus. The central portion, nucleus pulpous, is relatively soft and gelatinous, being composed of about 70 to 90% water. It has a high proteoglycan content and contains a significant amount of Type II collagen and chondrocytes. Surrounding the nucleus is the annulus fibrosus, which has a more rigid consistency and contains an organized fibrous network of approximately 40% Type I collagen, 60% Type II collagen, and fibroblasts. The annular portion serves to provide peripheral mechanical support to the disc, afford torsional resistance, and contain the softer nuclear portion while resisting its hydrostatic pressure.

Intervertebral discs, however, are susceptible to a number of injuries. Disc herniation occurs when the nucleus begins to extrude through an opening in the annulus, often to the extent that the herniated material impinges on nerve roots in the spine. The posterior and posterio-lateral portions of the annulus are most susceptible to attenuation or herniation, and therefore, are more vulnerable to hydrostatic pressures exerted by vertical compressive forces on the intervertebral disc. Various injuries and deterioration of the intervertebral disc and annulus fibrosus are discussed by Osti et al., Annular Tears and Disc Degeneration in the Lumbar Spine, *J. Bone and Joint Surgery*, 74-B(5), (1982) pp.678–682; Osti et al., Annulus Tears and Intervertebral Disc Degeneration, *Spine*, 15(8) (1990) pp. 762–767; Kamblin et al., Development of Degenerative Spondylosis of the Lumbar Spine after Partial Discectomy, *Spine*, 20(5) (1995) pp. 599–607.

Many treatments for intervertebral disc injury have involved the use of nuclear prostheses or disc spacers. A variety of prosthetic nuclear implants are known in the art. For example, see Bao et al., U.S. Pat. No. 5,047,055, which teaches a swellable hydrogel prosthetic nucleus. Other devices known in the art, such as intervertebral spacers, use wedges between vertebrae to reduce the pressure exerted on the disc by the spine. Intervertebral disc implants for spinal fusion are known in the art as well, as taught by Brantigan, U.S. Pat. Nos. 5,425,772 and 4,834,757.

Yet other approaches are directed toward replacement of the total disc, e.g., using a cage in the manner provided by Sulzer. Its BAK® Interbody Fusion System involves the use of hollow, threaded cylinders that are implanted between two or more vertebrae. The implants are packed with bone graft to facilitate the growth of vertebral bone. Fusion is achieved when adjoining vertebrae grow together through and around the implants, resulting in stabilization.

Yet others have described apparatuses and/or methods intended for use in disc repair, though none appear to have been further developed at all, let alone to the point of commercialization. See, for instance, Garcia (French Patent Appl. No. FR 2 639 823) and Milner et al. (International Patent Appl. No. WO 9531948). Both references differ in several significant respects from each other and from the method described below. For instance, neither reference even contemplates, let alone addresses, the manner in which the amount of delivered material can or should be carefully controlled in order to achieve a desired pressure within the disc space. Nor does either reference contemplate or address the ability to shunt an initial portion of a curing biomaterial, in the course of delivering the biomaterial to the disc space.

Applicant has described prosthetic implants formed of biomaterials that can be delivered and cured in situ, e.g., using minimally invasive techniques. See for instance, Applicant's U.S. Pat. No. 5,556,429 and published International Application WO 95/30388. Applicant's published International Application WO 97/26847 and International Application PCT/US97/20874 filed Nov. 14, 1997 (the disclosures of each of which are incorporated herein by reference) further describe, inter alia, the formation of a prosthetic nucleus within an intervertebral disc by a method that includes, for instance, the steps of inserting a collapsed mold apparatus (which in a preferred embodiment is described as a "balloon") through a cannula that is itself positioned through an opening within the annulus, and filling the balloon with a flowable biomaterial that is adapted to cure in situ and provide a permanent disc replacement. See also, Applicant's "Porous Biomaterial and Biopolymer Resurfacing System" (PCT/US99/10004), as well as "Implantable Tissue Repair Device (PCT/US99/11740), and "Static Mixer" (PCT/US99/04407) applications.

In the course of further developing and evaluating the methods and systems described previously, it has become apparent that various further improvements are desired, e.g., in order to permit the doctor to determine and achieve a suitable intervertebral distraction pressure in the course of surgery, and in turn, to permit the doctor to controllably and effectively deliver a desired quantity of biomaterial to the balloon.

BRIEF SUMMARY OF THE INVENTION

The invention provides a system that includes both a device (which, in turn, includes various unique components) and an in situ curable biomaterial, as well as a related method, for repairing (e.g., replacing in whole or in part) an intervertebral disc by delivering and curing the biomaterial in situ. The system can be used to implant a prosthetic total disc, or a prosthetic disc nucleus in a manner that leaves the surrounding disc tissue substantially intact. In a preferred embodiment, the method includes the steps of providing, inserting, and positioning a device that includes an inflatable balloon into the intervertebral disc space. Once positioned, the balloon is filled with a curable biomaterial until the balloon expands to the desired size and dimensions, whereupon the biomaterial is then permitted to fully cure in situ to form a final prosthesis having the desired geometry and dimensions to substantially provide or restore the desired anatomy and function of the disc. Optionally, and preferably, the system of the invention is adapted for minimally invasive use.

In various preferred embodiments, the method and apparatus of the present invention provide a variety of improvements over the various approaches previously described, e.g., in that the apparatus can permit the doctor to determine a suitable endpoint for biomaterial delivery (e.g., by controlling distraction and/or biomaterial delivery pressure), and in turn, to deliver a desired (e.g., predetermined) quantity of biomaterial to the balloon in order to achieve improved polymer cure and implant characteristics.

In one preferred embodiment, the biomaterial delivery pressure is itself used to determine the endpoint. Such a system includes a device for forming an intervertebral disc prosthesis in situ, the device comprising:

a) a collapsed balloon (e.g., compliant or noncompliant) adapted to be positioned within a disc space in order to provide, upon being filled and inflated with biomaterial, one or more exterior tissue-contacting surfaces and one or more interior cavities formed by corresponding interior surfaces, at least one of the interior cavities being adapted to receive a curable biomaterial;

b) first and second lumen, each having proximal and distal ends, with the proximal (i.e., patient) ends of each lumen coupled, or adapted to be coupled, in fluid and/or gaseous communication with an interior cavity of the balloon;

c) one or more adaptors, preferably including a fluid control valve, associated with the first lumen and adapted to operably and controllably connect and provide fluid communication between the distal end of the first lumen and a flowable biomaterial delivery apparatus; and d) one or more adaptors associated with the second lumen and adapted to operably and controllably affect fluid and/or gas pressure within the balloon in the course of its filling.

Optionally, and particularly for use in total disc replacement, a system of the invention further includes endplates and fixation components in combination with such a device. The balloon material can be either substantially compliant, in that it can also be expanded in the course of being inflated, or it can be substantially non-compliant under the conditions (particularly pressure) involved in its use.

A corresponding system of this invention, in turn, comprises:

a) one or more devices of the types described herein, b) one or more biomaterial sources, at least one of the sources comprising a plurality of parts adapted to be mixed and delivered to the balloon portion of the device in order to be cured in situ within the disc space; and c) one or more corresponding biomaterial delivery devices, each adapted to mix a plurality of biomaterial parts and deliver the curing biomaterial(s) to the cavity of the balloon portion.

In such a preferred embodiment, the system can include a variety of optional features, including an endpoint monitor adapted to provide the surgeon with an indication of a suitable endpoint for biomaterial delivery. In one preferred embodiment, for instance, the endpoint monitor includes a pressure monitor associated with a lumen (preferably the first lumen) of the device, for use in detecting and/or determining a suitable endpoint by determining the distraction pressure brought about by the delivery of biomaterial within the disc space.

In one such embodiment, the system includes a pressure monitoring component adapted to determine the pressure of biomaterial being delivered within the balloon, by monitoring a representative sample of the biomaterial external to the body. In a particularly preferred embodiment, Applicants have addressed the problem of attempting to make an accurate pressure determination under these complicating conditions—first, at a site remote from the balloon itself (e.g., a biomaterial path outside the body), though in a manner representative of the pressure within the balloon, and second, providing prompt, accurate, and substantially real-time pressure readings in a system in which the biomaterial is not only continually curing, but may be curing at different rates at different points within the system (e.g., depending on the time and distance between those points and the initial mixing of biomaterial parts). In one embodiment, Applicants have solved these problems by the unique arrangement and use of a pressure gauge and/or sensor as presently described.

The biomaterial delivery endpoint monitor can be based on parameters other than, or in addition to delivery or distraction pressure, such other parameters being useful either alone or in conjunction with each other. Such endpoint monitors include, for instance, those based on the volume of biomaterial delivered, and/or means for measuring and/or visualizing (e.g., by C arm or interoperative MRI) of the extent of distraction achieved.

Optionally, or in addition to the endpoint monitor, the system can include an adaptor for use in shunting biomaterial between the biomaterial delivery device and the balloon. Such an adapter can be associated with the first lumen of the device, for instance, in order to shunt either an initial portion of the biomaterial and/or to terminate the flow of biomaterial from the delivery device to the balloon by redirecting (e.g., shunting) the flow in another direction.

In another aspect, the present invention provides a biomaterial in the form of a curable polyurethane composition comprising a plurality of parts capable of being aseptically processed or sterilized, stably stored, and mixed at the time of use in order to provide a flowable composition and initiate cure, the parts including: (1) a quasi-prepolymer component comprising the reaction product of one or more polyols (e.g., polyether or polycarbonate polyols), and one or more diisocyanates, and optionally, hydrophobic additives, and (2) a curative component comprising one or more polyols, one or more chain extenders, one or more catalysts, and optionally, other ingredients such as antioxidants, and dyes. Upon mixing, the composition is sufficiently flowable to permit it to be delivered to the body, and there fully cured under physiologically conditions. Preferably, the component parts are themselves flowable, or can be rendered sufficiently flowable, in order to facilitate their mixing and use.

Another aspect of the invention involves a method of providing an intervertebral disc or nucleus prosthesis. In a particularly preferred embodiment, the method comprises the steps of:

a) preparing and accessing the disc
  i) gaining access to the intervertebral disc;
  ii) creating a space by removing damaged or diseased tissue from disc, e.g., by performing a discectomy;
  iii) providing a system of the present invention, including a device comprising an inflatable balloon portion, optionally endplates or other suitable means for retaining the balloon in its desired position, and one or more biomaterial delivery devices and corresponding biomaterial sources;
  iv) inserting the inflatable balloon component of the device into the created disc space (e.g., into the nuclear portion of the disc), for instance, by the use of an introducing cannula that contains the balloon in a compact form within a proximal portion thereof, and preferably, that provides a proximal end adapted to be secured to tissue within the disc space;
  v) introducing and positioning the balloon within the space, e.g., by securing the cannula within the disc space, and retracting the introducing cannula and/or extending the compacted balloon from the introducer into the space, preferably in a manner and under conditions suitable to permit the balloon to conform itself, at least in part, to the available space;
b) delivering the biomaterial by:
  i) drawing a vacuum on the balloon, with fluid communication to the biomaterial in a closed position;
  ii) mixing a plurality of biomaterial parts in order to initiate cure, and filling the balloon with the mixed and curable, yet flowable, biomaterial, preferably after shunting an initial portion of the mixed biomaterial;
  iii) permitting the biomaterial to inflate (and optionally expand) and fully cure within the balloon to form a prosthesis, wherein the filling and expansion of the balloon and the curing of the biomaterial are performed by controlling the fluid pressure of the biomaterial within the device throughout the procedure, optionally and preferably within a time period and with a pressure sufficient, in whole or in part, to achieve and/or maintain intervertebral distraction; and
c) removing unnecessary portions or components of the system from the surgical site, e.g., severing and removing portions of the device extending beyond the disc site or annulus.

Accordingly, the biomaterial delivery apparatus delivers a flowable, curable biomaterial into the first cannula, thereby filling the balloon, and forcing air and excess biomaterial out through the second cannula. The fluid pressure within the cannulas and the balloon can be controlled by adjusting the amount and/or rate of fluid exiting the second cannula, in combination with controlling the amount of fluid inlet pressure by way of the fluid control valve and force exerted to expel the biomaterial from the delivery apparatus.

The invention also includes a kit containing the system of the invention and further comprising a biomaterial source and biomaterial delivery apparatus. The kit can further include a cannula insertion guide wire, a device for severing the cannula from the balloon (such as a co-axial cutting instrument), and devices for facilitating intervertebral disc tissue repair (such as an annular plug as taught by Applicant's U.S. Ser. No. 09/086,848), the disclosure of which is incorporated herein by reference.

Also included in the invention is a prosthesis formed in situ using the device, system and method of the invention. In one embodiment, the prosthesis is provided within the annulus and in apposition to the natural or augmented (e.g., prosthetic) endplates of a disc. In an alternative embodiment, the prosthesis is provided in a manner that substantially replaces the natural annulus, and optionally includes one or more prosthetic endplate components affixed and in apposition to natural bone.

DETAILED DESCRIPTION OF THE INVENTION

The invention includes a system, including device and biomaterial, as well as a method of using such a system for repairing an intervertebral disc using an in situ curable biomaterial. The invention can be used to implant a prosthetic nucleus while leaving the surrounding disc tissue substantially intact. In an alternative embodiment, the invention can be used to replace a total disc, or some combination of annulus and nucleus repair/replacement. The phrase intervertebral disc prosthesis is used generically to refer to all of these variations. Optionally and preferably, the device and system of the invention are adapted for minimally invasive use.

Figure 1:
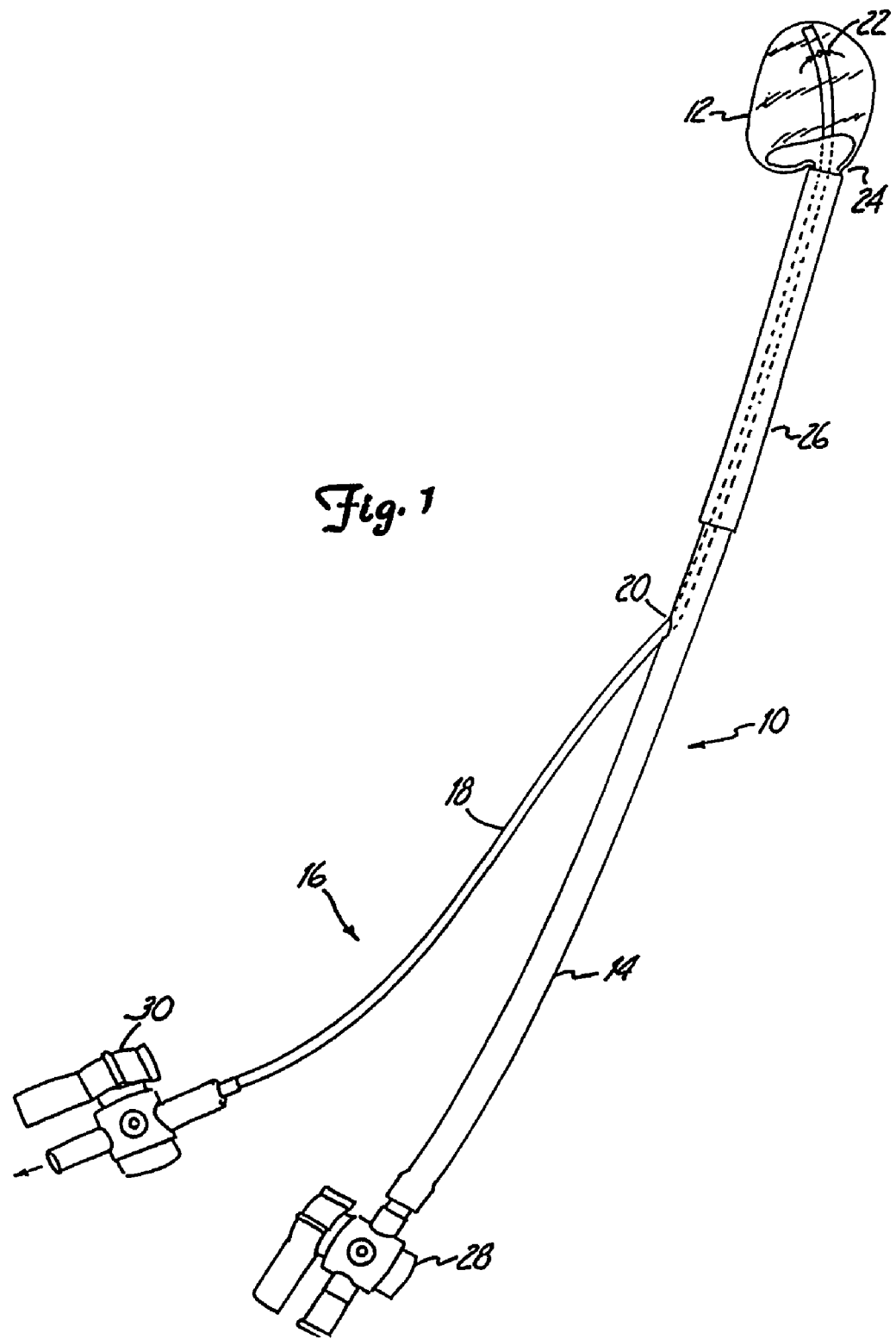
FIG. 1 shows a top plan view of a mold apparatus including a balloon cavity and biomaterial delivery conduit for use in intervertebral disc replacement.

An inflatable device for use in intervertebral disc repair will be described with reference to the Drawing, and in particular FIGS. 1 through 5. In FIG. 1, certain components of an apparatus (10) are shown having balloon portion (12) and biomaterial conduit (14). The balloon is dimensioned to be positioned within the annular shell following discectomy, and there filled with biomaterial in order to provide a replacement disc.

In the particular embodiment shown, conduit (14) includes a venting system (16) that includes air passageway (18) passing from a distal point along the conduit, into and through its wall (20) in order to pass along the interior of the conduit. Air passageway (18) terminates at a point at or near the proximal end of balloon (12), where it can be used to provide gas or other fluid under pressure (e.g., in order to position the balloon and/or distract the joint) and where it can optionally be used to vent gas (e.g., air) within the balloon as the balloon is filled with biomaterial. As shown, the air passageway (18) is preferably provided with one or more vent holes (22) at locations within the balloon, which serve to facilitate the delivery of biomaterial by improving venting of gas from within the balloon. Conduit (14), including the air passageway, can be severed from balloon portion at or near the point (24) where they attach to or pass through the wall of the balloon. In this manner the conduit can be removed from the balloon as or after the biomaterial cures.

Figure 2:
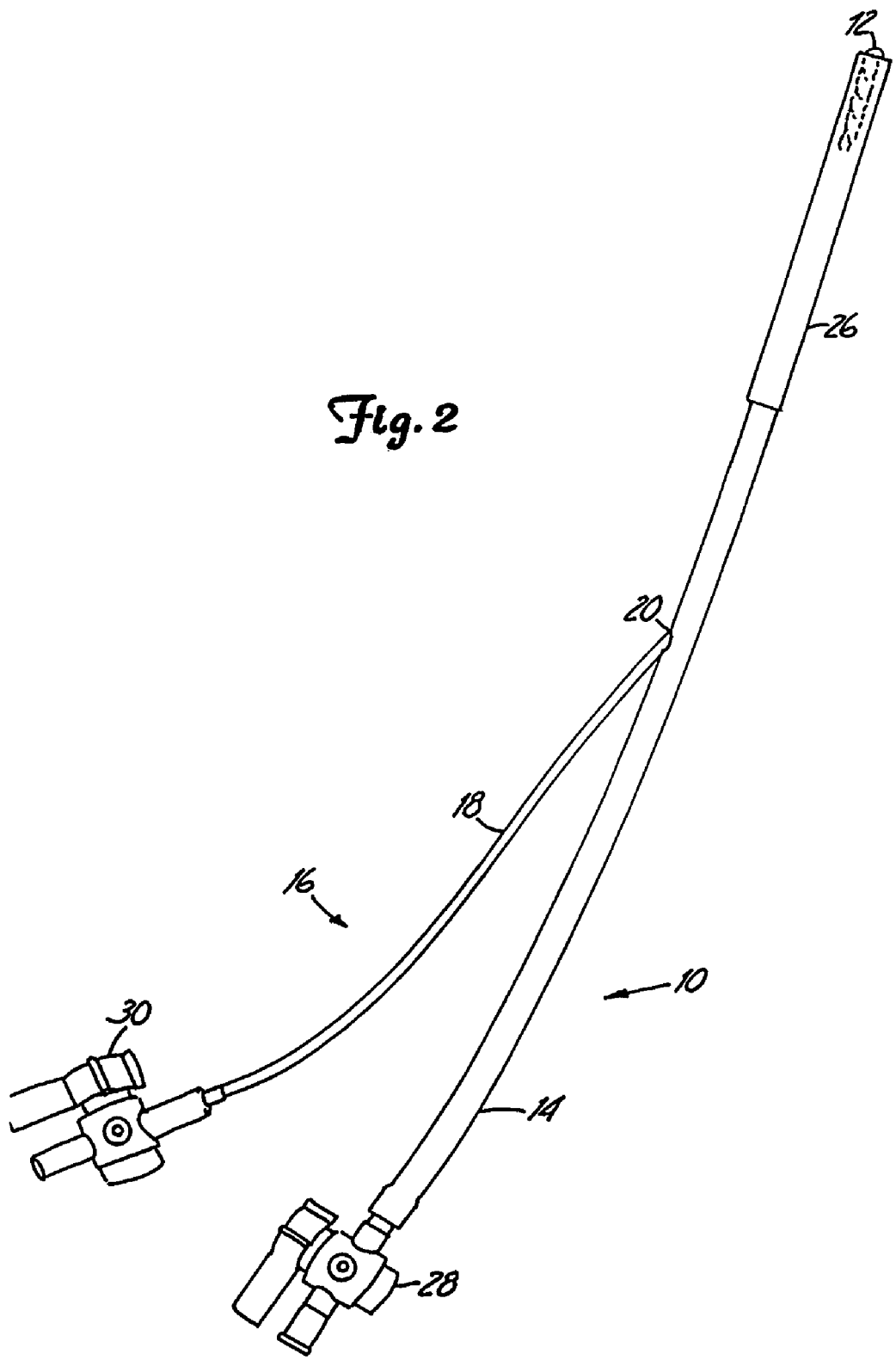
FIG. 2 shows the apparatus of FIG. 1 with the balloon in its collapsed form contained within an outer sheath, suitable for insertion and positioning within the disc space.

As shown in FIG. 2, the balloon is preferably provided in a form collapsed or rolled within sheath (26), which can be docked on the annulus over the incision site or partially inserted into the annular incision to guide the balloon insertion into the disc space. Sheath (26), conduit (14) and air passageway (18) can each be prepared from materials commonly used for such purposes, such as Nylon catheters, and suitably dimensioned to provide the respective functions. The conduit portion (14), for instance, will preferably be about 10 cm to about 70 cm in length, depending on the surgical approach and technique, and about 0.1 cm to about 1 cm, and more preferably about 0.3 cm to about 0.7 cm in outer diameter. The air passageway (18), in contrast, will typically be about 1 mm to about 3 mm in outer diameter, and of sufficient length to extend about 2 cm to about 4 cm beyond the proximal end of the conduit. The balloon, in turn, will typically be about 1.5 cm to about 6 cm in its longest dimension, about 1 cm to about 4 cm in width, and about 0.5 cm to about 1.5 cm in height, once filled with biomaterial. Both the biomaterial conduit (14) and air passageway (18) are preferably provided with controllable and adjustable valves (28) and (30), for use in adjusting the flow of biomaterial and fluid, respectively, between the two.

Preferably, air passageway (18) can be provided such that it terminates at point substantially at or near where it meets the balloon, i.e., such that it does not extend into the balloon itself. In this manner it has been found that the balloon can still be adequately evacuated in a manner that avoids the need to keep the distal portion of the air passageway permanently encased in cured biomaterial within the implant.

In a related embodiment, the mold apparatus, or a kit that contains or is adapted for use with such a mold apparatus, can include means for positioning the balloon in situ, e.g., in the form of a vascular guide wire that can be placed through the delivery conduit itself, or preferably through an air passageway that terminates at or near the point of contact with the balloon. The guide wire can be designed to substantially assume the curved contour of the extended but unfilled balloon, and to provide a plane of orientation, in order to both facilitate placement of the balloon and provide an outline of the periphery of the balloon in position and prior to filling. Thereafter, the guide wire can be removed from the site prior to delivery of the biomaterial and air evacuation. The use of a guide wire in this manner is particularly facilitated by the use of an air passageway that is unconnected to, and positioned outside of, the biomaterial conduit.

Optionally, and in order to facilitate the placement of the collapsed balloon within a sheath, the invention further provides a rod, e.g., a plastic core material or a metal wire, dimensioned to be placed within the balloon, preferably by extending the rod through the conduit. Once in place, a vacuum can be drawn on the balloon through the air passageway in order to collapse the balloon around the rod. Simultaneously, the balloon can also be twisted or otherwise positioned into a desired conformation to facilitate a particular desired unfolding pattern when later inflated or filled with biomaterial. Provided the user has, or is provided with, a suitable vacuum source, the step of collapsing the balloon in this manner can be accomplished at any suitable time, including just prior to use. In certain embodiments it will be desirable to collapse the balloon just prior to its use, e.g., when using balloon materials that may tend to stick together or lose structural integrity over the course of extended storage in a collapsed form. Alternatively, such balloon materials can be provided with a suitable surface coating, e.g., a covalently or noncovalently bound polymeric coating, in order to improve the lubricity of the surface and thereby minimize the chance that contacting balloon surfaces will adhere to each other.

Figure 6:
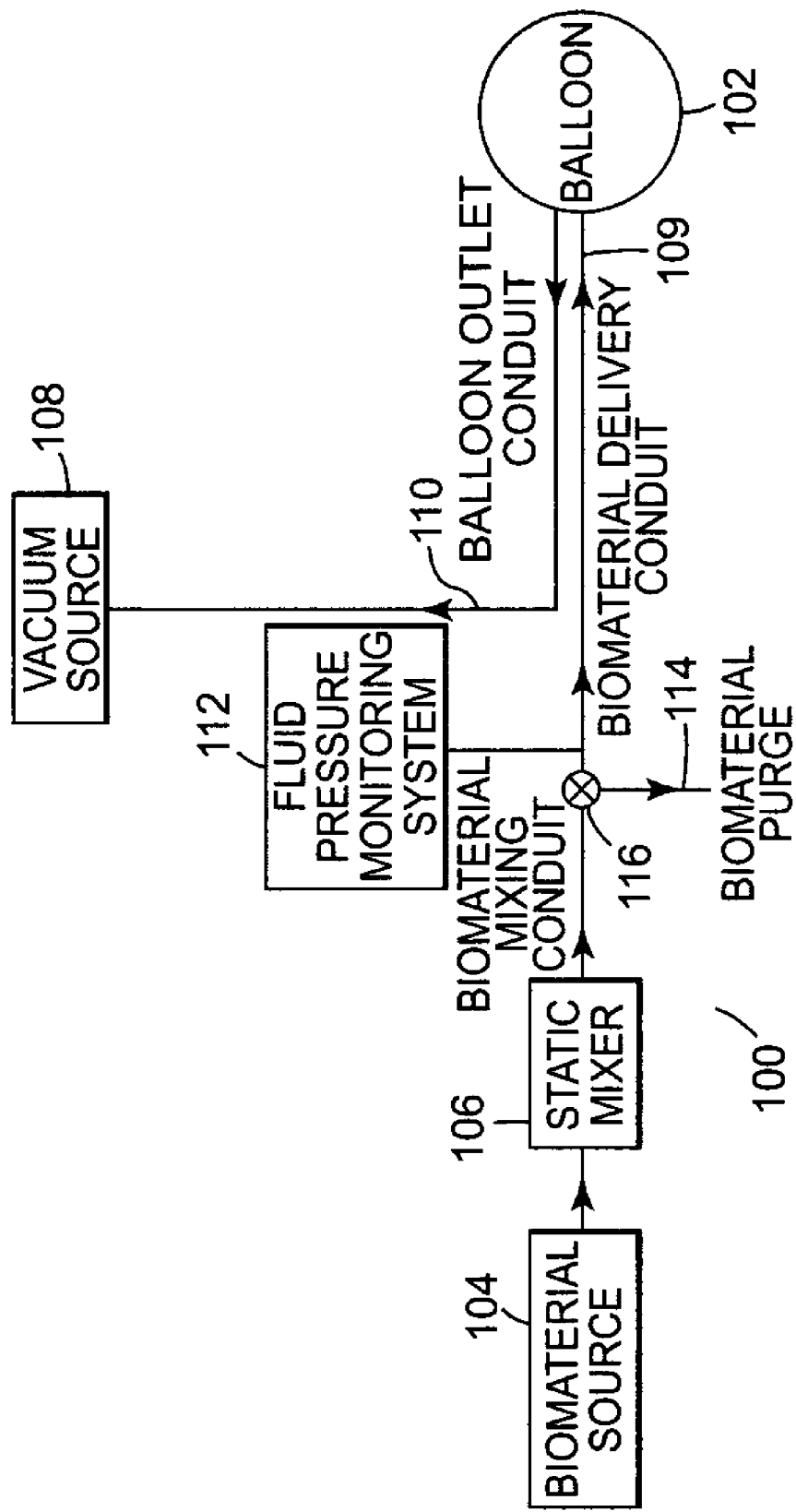
FIG. 6 is a fluid circuit diagram illustrating one embodiment of a preferred system according to the invention.

FIGS. 6–11 will be described with respect to various additional and optional embodiments and features associated with an exemplary system, including device, of this invention. FIG. 6 is a fluid circuit diagram illustrating one embodiment of a preferred system according to the invention. It can be seen that the system includes a balloon component 102 as well as a biomaterial source 104 and static mixer 106 for use in mixing a plurality of biomaterial components at the time of delivery and use. The circuit as shown also includes a vacuum source 108 and associated lumen 110, as well as a fluid pressure monitor 112 and purge path 114. Various functions are controlled by the use of three-way control valve 116, which can be used to access the various lumen in the course of controlling and/or monitoring pressure and the flow of biomaterial to the balloon.

Figure 7:
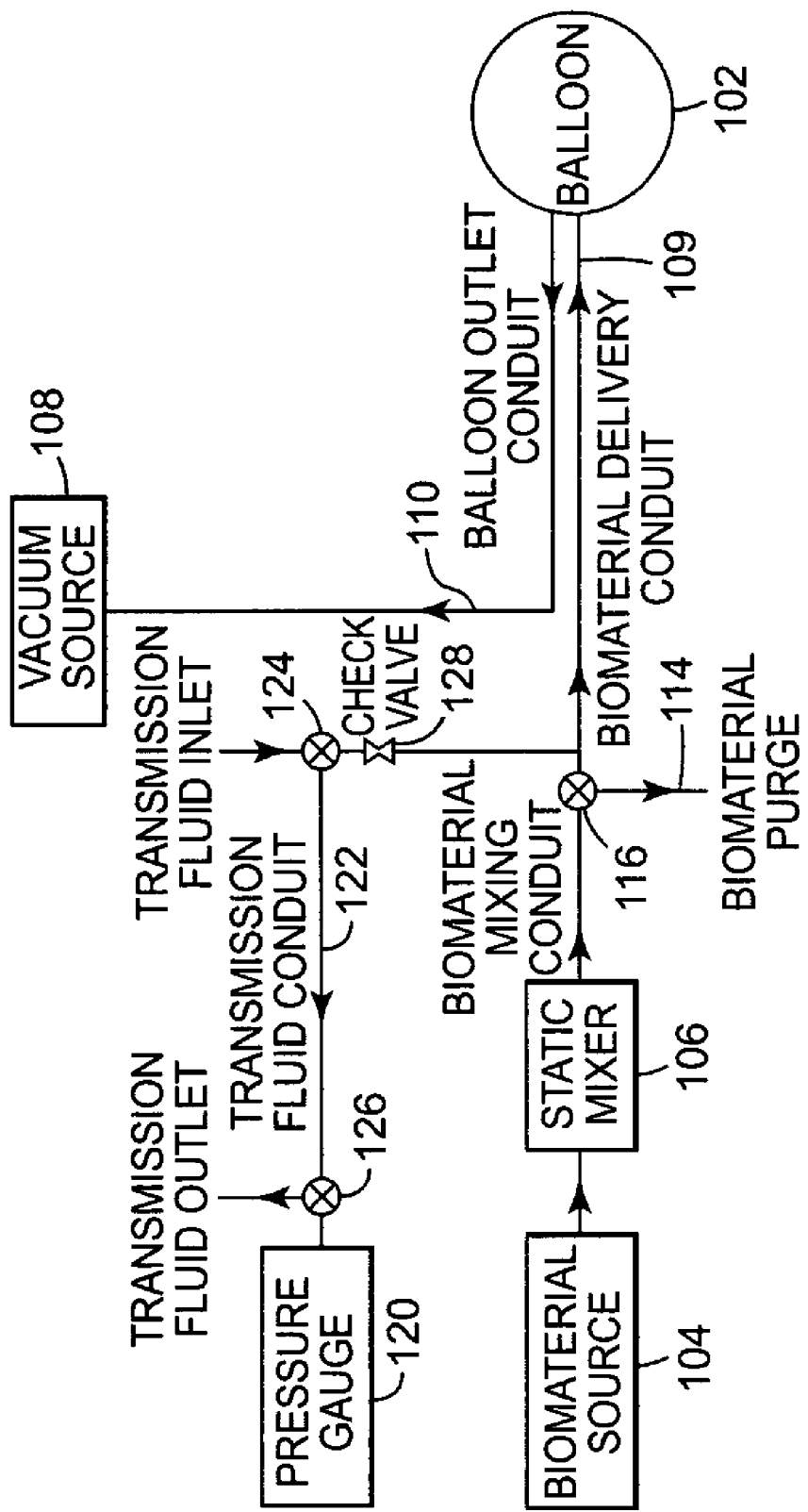
FIG. 7, in turn, shows a circuit diagram as depicted in FIG. 6, though including certain components of the pressure monitor.

FIG. 7, in turn, shows a circuit diagram as depicted in FIG. 6, though including certain components of the pressure monitor, including a pressure gauge 120, fluid conduit 122 having both inlet 124 and outlet 126 ports, was well as a check valve 128.

Figure 8:
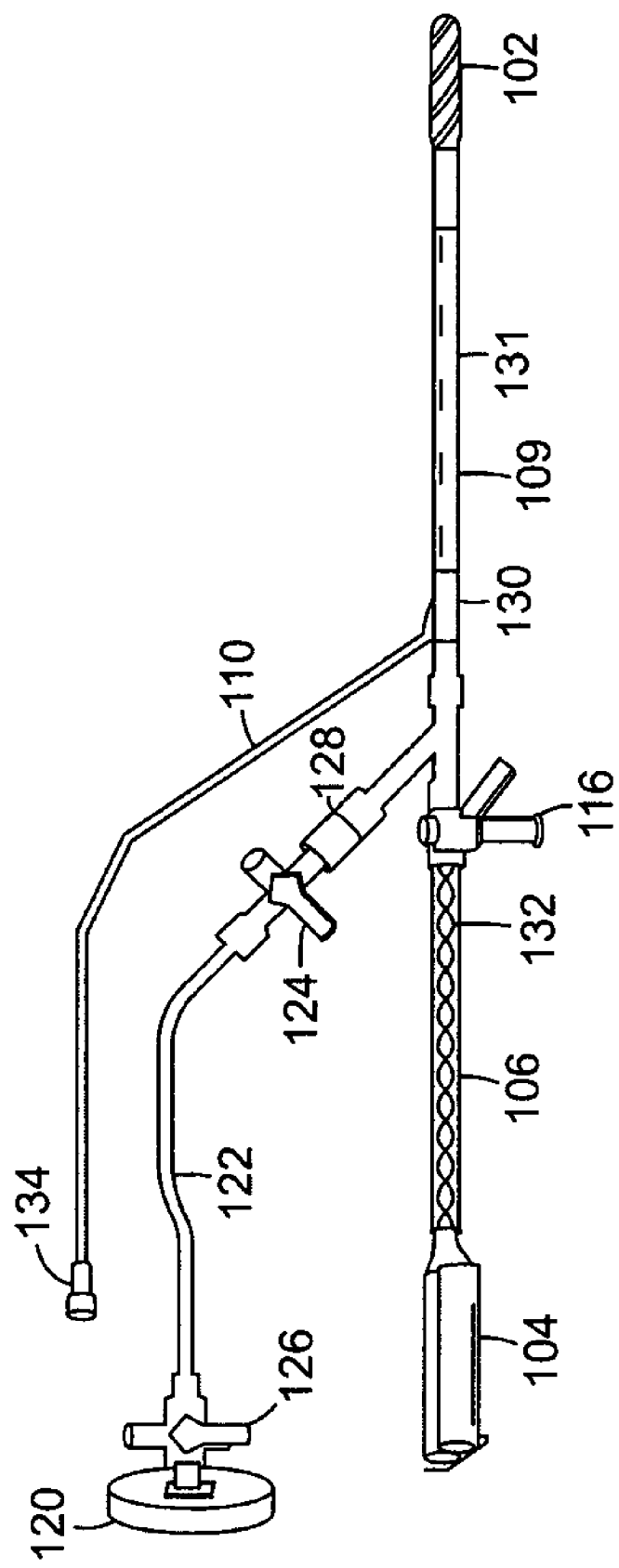
FIG. 8 is an illustration of a preferred embodiment of the device of this invention.

FIG. 8 is an illustration of a preferred embodiment of the device of this invention, in which balloon 102 (shown in its extended position) is attached to the proximal (i.e., patient) end of a cannula 130 that includes within it both a biomaterial delivery lumen 109 and vacuum lumen 110 having a distal adapter 134 for attachment to a suitable vacuum source (not shown). Also attached to a distal end of the device is a biomaterial source 104, in the form of a two-part syringe pack 104, and a static mixer path 106 having a plurality of (approximately 16) mixer elements 132 therein. Biomaterial flow throughout the device is controlled by control valve 116, which permits the flow to be controlled as between a purge path (114 in FIG. 7) and the delivery path (109) of FIG. 7.

Also shown is an endpoint monitor in the form of a pressure monitor adapted to provide a remote but valid indication of the biomaterial delivery (and in turn, distraction) pressure within the balloon. The pressure monitor includes a pressure gauge 120 as well as a transmission fluid conduit 122 having both inlet 124 and outlet 126 ports, as well as a check valve 128.

Figure 9:
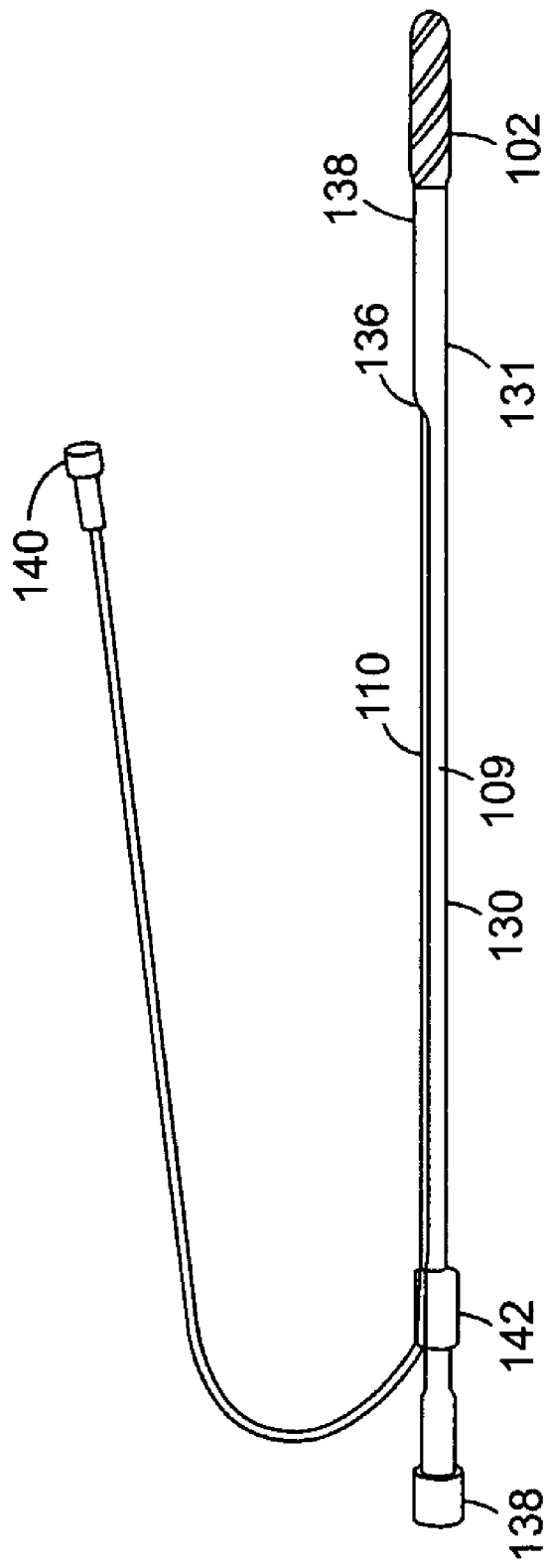
FIG. 9 shows an isolated view of the balloon and related lumen components of the device shown in FIG. 8.

FIG. 9 shows an isolated view of the balloon and related lumen components of FIG. 8, in which balloon 102 is shown attached to the proximal end of cannula 130, which in turn includes both the vacuum lumen 110 (here, as a separate and substantially smaller tube within the cannula) and biomaterial delivery lumen 109 (as the remaining lumen within the cannula itself). Also shown is a retractable sheath 131, described below, for use in covering the balloon and optionally securing the device to tissue in the course of positioning the balloon. It can be seen that in this particular, and preferred, embodiment the proximal portion of vacuum lumen ends at a point 136, that is substantially distal to the attachment point 138 of the balloon to the cannula. Also shown are an adaptor 138 for use in attaching this component to the three-way valve 116 and another adaptor 140 for use in attaching the vacuum conduit to a vacuum source. The distal portion of vacuum conduit 110 separated from its position within the cannula at cuff 142, in order to permit the distal portion to be moved to various locations, including out of the surgical field, with the balloon and remaining cannula kept in place.

Figure 10A:
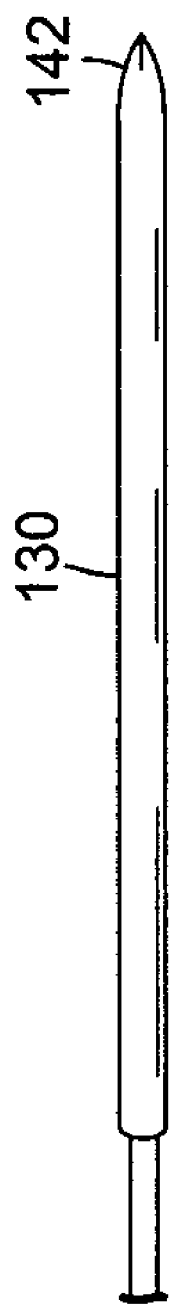
FIGS. 10a and 10b show the proximal end of a cannula with the balloon in both its unextended and extended positions respectively.
Figure 10B:
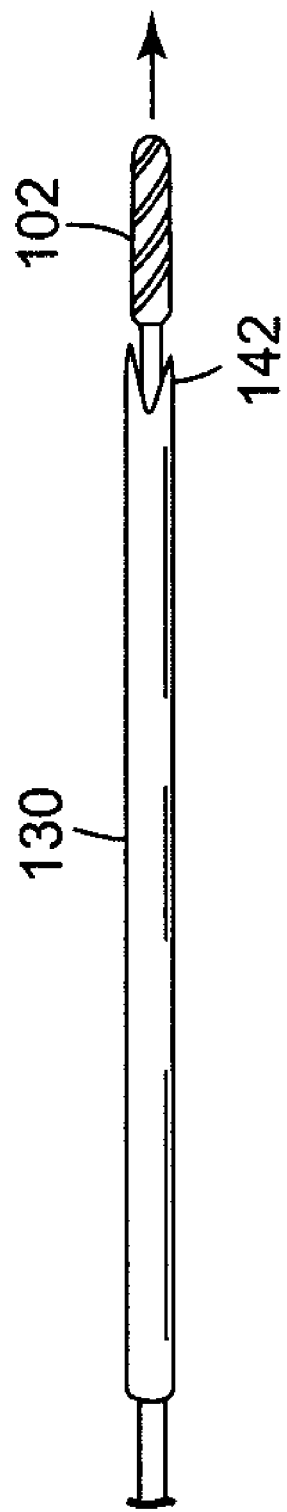

FIGS. 10a and 10b show the proximal end of a cannula with the balloon in both its unextended and extended positions respectively. The proximal end of the cannula is provided in a suitable manner (here with fluted portions 142) that permit secure placement and/or attachment of the proximal end to natural tissue in the course of introducing and positioning the balloon. The fluted portions are initially provided in a compact condition (FIG. 10a), and are expanded by extending the balloon therethrough. FIGS. 11 through 14 show side views of the use of various endplate designs for use in total disc repair, and will be discussed in greater detail herein.

A system of the present invention includes a device for forming a total or nuclear intervertebral disc prosthesis in situ. A device of the present invention includes one or more inflatable balloons (occasionally also referred to herein as "molds" or "mold cavities") adapted to provide an exterior tissue-contacting surface and an interior cavity, formed by an interior surface and adapted to receive a curable biomaterial.

Mold cavities of the present invention, e.g., the balloon of FIG. 1, can be formed by any suitable means. In one embodiment, the balloon is fabricated by dip-coating a suitably shaped mandrel into a curable polymer solution. Applicants have discovered that a mandrel ideally suited for this purpose can be prepared from a remoldable bismuth-based material. Examples of suitable materials include low melting point fusible materials, such as bismuth alloys that are commercially available from a number of sources.

Figure 3:
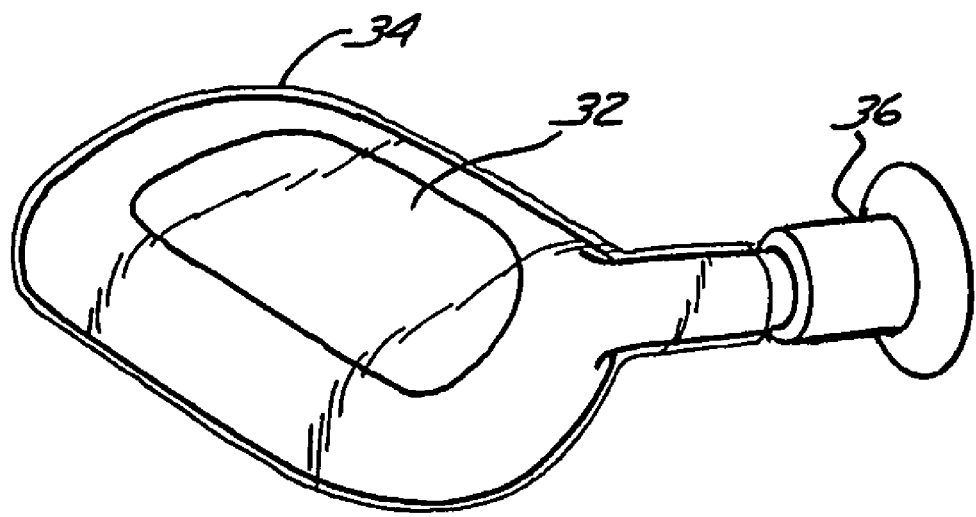
FIG. 3 shows a mandrel used for forming the balloon of FIG. 1 by dip-coating the mandrel in a suitable solution of curable polymer.
Figure 4:
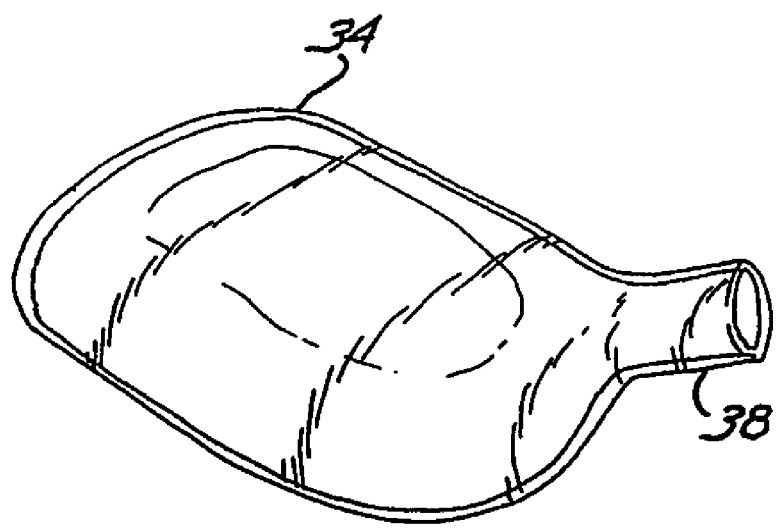
FIG. 4 shows a balloon as formed upon the mandrel shown in FIG. 3

A preferred mandrel will be described with reference to FIGS. 3 and 4. FIG. 3 shows a mandrel 32 covered with newly formed balloon 34 and held in chuck 36. The solid mandrel 32 is used to form a balloon by dipcoating it in a suitable solution (not shown) as described herein. Once cast, the mandrel can be melted in order to remove it from the balloon by dipping the combination in water at about 120 degrees C. for about 5 to 15 minutes. As the mandrel liquefies it can be poured and/or squeezed out of the balloon and reformed for further use. FIG. 4 shows the resultant balloon 34, after removal of the mandrel, formed by this process. In the preferred embodiment shown, the balloon retains an integral stem portion 38 that provides an attachment site for the conduit shown in FIG. 1.

A preferred balloon provides an optimal combination of such properties as extendibility and strength. Typically, a non- or less extendible (and in turn, substantially non-compliant) material, such as polyethylene and polyester, would have better strength. A non-compliant balloon with high strength has the advantages of being able to withstand high injection pressure and maintaining its pre-determined volume and shape without applying too much pressure on the annulus during the balloon inflation. In this respect, a balloon that is substantially non-compliant, but strong, can be used to distract the disc space upon delivery of biomaterial, and by virtue of the biomaterial delivery pressure. One of the disadvantages of using a non-compliant balloon includes potential poor confirmation of balloon size and shape with the cavity size and shape.

In one embodiment, the balloon is constructed from a porous material where the pore sizes retain the curable biomaterial, but permit the passage of gases from the inside of the balloon to the outside of the balloon. Such a porous balloon would preferably have pore sizes of about 50 micrometers to about 1000 micrometers, and more preferably about 100 micrometers to about 500 micrometers.

Alternatively and preferably, materials with significant extendibility (and in turn, increased compliance) are also suitable for the balloon material. An advantage of using elastomeric materials within or as the balloon material includes better conformity between the filled balloon and the disc cavity and therefore better stress distribution towards the annulus. Examples of compliant materials for use in preparing balloons of the present invention include, for instance, block copolymers such as castable thermoplastic polyurethanes, for instance those available under the tradenames CARBOTHANE (Thermedics) ESTANE (Goodrich), PELLETHANE (Dow), TEXIN (Bayer), Roylar (Uniroyal), and ELASTOTHANE (Thiocol), as well as castable linear polyurethane ureas, such as those available under the tradenames CHRONOFLEX AR (Cardiotech), BIONATE (Polymer Technology Group), and BIOMER (Thoratec).

Preferred compliant polymers provide an optimal combination of such properties as flexibility under static and dynamic conditions, tensile strength, elongation, tensile modulus, ductility, stability and durability, compliance, porosity, and patency. See generally, M. Szycher, *J. Biomater. Appl.* "Biostability of polyurethane elastomers: a critical review", 3(2):297–402 (1988); A. Coury, et al., "Factors and interactions affecting the performance of polyurethane elastomers in medical devices", *J. Biomater. Appl.* 3(2): 130–179 (1988); and Pavlova M, et al., "Biocompatible and biodegradable polyurethane polymers", *Biomaterials* 14(13):1024–1029 (1993), the disclosures of which are incorporated herein by reference.

In one preferred embodiment, the balloon provides both elastic properties and non-elastic properties at different regions. In one such design, the lateral wall of the material is non-compliant (or having a compliance value significantly higher than the delivery pressure so it is virtually not stretched) and the superior and inferior walls are compliant (or having a compliance value significantly low than the delivery pressure). With this design, during polymer delivery and distraction, the distraction force is essentially applied in vertical direction without exerting high expansion force on the surrounding annulus. This design is particularly useful for patients with pre-damaged annulus.

Given the present description, those skilled in the art will be able to employ conventional methods, such as casting, for forming balloons and similar molds of this invention. See, for instance, "Casting", pp. 109–110, in Concise Encyclopedia of Polymer Science and Engineering, Kroschwitz, ed., John Wiley & Sons (1990). Balloons can be cast to achieve any desired final thickness, preferably on the order of 0.005 inches (0.01 cm) to about 0.015 (0.05 cm) inches thick, and preferably between about 0.008 inches (0.02 cm) to about 0.012 inches (0.03 cm). The balloon itself is preferably cleaned, e.g., by the use of suitable solvents.

Optionally, reinforcing materials such as meshes formed of natural or synthetic materials can be incorporated into the balloon, e.g., by layering them onto various portions while still wet, and covering the mesh with subsequent dip coats. A mesh can be cut in a form sufficient to extend around the perimeter of the balloon, for instance, in order to provide added strength in the course of filling the balloon and distracting the space. Suitable materials for preparing meshes include polyamide (e.g., NYLON), polyester (e.g., tradenames DACRON and HYTREL), polyethylene, and polypropylene, as well as liquid crystal polymers available under the tradename VECTRA.

The various components of a mold apparatus can be prepared and assembled using techniques within the skill of those in the art. For instance, a balloon, conduit and air passageway can be individually prepared and assembled by attaching the balloon to an end of the conduit, e.g., by gluing or sonic welding, and positioning the air passageway within or alongside the conduit and extending into the balloon. Thereafter the sheath can be applied to the conduit and slid over the balloon in its collapsed or rolled configuration. Other materials or means can be incorporated into the apparatus, such as radioopaque portions, to facilitate the surgeon's ability to orient the balloon in situ. Also, various joints and junctures between the parts of the apparatus can be sealed by the use of suitable adhesives or other materials.

In a preferred embodiment, a device of the present invention includes a mold apparatus in the form of a balloon component that provides both an exterior tissue-contacting surface and an interior cavity, formed by the interior surface, for the receipt of curable biomaterial. The balloon is preferably inflatable and expandable, e.g., by the delivery of gas under pressure and/or by the delivery of fluid materials, such as inert gas or fluid, or by the biomaterial itself.

In a particularly preferred embodiment, the inflatable balloon component of the device can be prepared from a variety of rupture-resistant materials, as described herein, adapted to inflate in response to fluid pressure exerted from within the balloon, and in response to the flowable uncured biomaterial applied to the device. The balloon can be composed of either a single layer of material (expandable or nonexpandable) material, or alternatively, two or more layers of materials having the same or different levels of expandability. The shape, size, thickness, and dimensions of the balloon are selected such that when filled with the biomaterial, the balloon complies with the interior geometry of the enucleated disc or nuclear cavity within which the balloon is to be positioned, as well as the particular patient's needs. Typically, when filled, the balloon will have a semi-flattened ovoid configuration, wherein the length and width of the balloon are greater than its height, and length greater than width.

Particularly preferred balloon materials include, but are not limited to, polymeric materials such as aliphatic or aromatic polycarbonate-based and non-polycarbonate-based polyurethanes. Preferred polyurethanes are aliphatic polycarbonate-based polyurethanes, such as Carbothane™

(available from Thermedics, Woburn, Mass.), and aromatic polycarbonate-based polyurethanes, such as Chronoflex™ (available from CT Biomaterials, Woburn, Mass.). Also useful are polyether-based polyurethanes such as Pelethane™ (available from Dow Plastics, The Dow Chemical Company, U.S.A.). To enhance the biostability of the balloon material, one also can use polyurethanes which contain silicone, such as polydimethylsiloxane (PSX) in the soft segment. Examples of these silicone containing polyurethanes are available under the tradenames Pursil™ (polyether-based) and Carbosil™ (polycarbonate-based), and are available from Polymer Technology Group (Berkeley, Calif.). In a further embodiment, the balloon material can comprise two or more different polycarbonate-based polyurethanes, two or more different polyether-based polyurethanes, and mixtures thereof.

When an expandable balloon includes two or more layers, different polymeric materials having different physical and functional properties can be used for each individual layer. Preferred is a combination whereby the inner layer is formed of a polymeric material that provides improved exotherm (heat)-resistant and/or rupture resistant properties (as compared to the outer layer), and the outer layer is formed of a polymeric material that provides improved resistance to physical damage and/or puncture forces (as compared to the inner layer). More particularly, the inner layer of the balloon preferably exhibits an optimal combination of such properties as heat resistance (sufficient to withstand exotherm temperatures of the curing biomaterial without detrimental effect), tensile strength, elongation failure, and rupture resistance, and in turn, will generally be more rigid as compared to the outer layer of the balloon. In turn, the outer layer of the balloon preferably exhibits an optimal combination of such properties as puncture resistance and higher tolerance for physical contact damage, and will generally be softer and more compliant as compared to the inner layer.

Also optionally, the various materials and/or portions (e.g., interior or exterior surfaces) of the balloon can be treated with materials to provide a different desired effect (e.g., hydrophobicity, hydrophilicity, balloon/biomaterial adhesion or bonding, lubricity, tissue ingrowth, and biocompatibility). Methods and compositions useful for coating such materials are available and will become apparent to those of skill in the art, given the present description. One example of a suitable composition and layer combination is a two-layered balloon comprising an inner, exotherm heat-resistant layer formed of an aliphatic, polycarbonate-based polyurethane such as Carbothane 55D and an outer, puncture-resistant layer formed of a mixture of 70% Chronoflex and 30% Carbothane.

Balloon wall thickness will vary according to the materials used. When a double-layer balloon is used, the outer layer double wall thickness will be from about 0.003 inches to about 0.015 inches. Likewise, the inner layer double wall thickness will range from about 0.003 to about 0.015 inches. Whichever combination of inner and outer layer thickness is used, it is preferred to have a combined single wall thickness of from about 0.006 inches to about 0.03 inches.

Given the present description, one of ordinary skill in the art will be able to select the various polymers, layering structure, and balloon thickness, including combinations thereof, in order to optimize results of the implantation and prosthesis according to the patient's condition. Balloon material properties can be modified by selecting certain polymers and polymer formulations which produce various effects with regard to a) molecular orientation (which refers to the process by which the polymer chains are preferentially aligned in one or more directions, which can increase the strength and beneficial effect compliance of the material) and/or b) crystallinity (which refers to the process of forming crystals which serve to lock the molecular orientation in place, and the degree of crystallinity and/or crystalline morphology can have beneficial effects on material strength, compliance, toughness/tear resistance).

For more compliant balloons, particularly preferred balloons of the present invention exhibit a compliance of between about 0.0005 inch/psi (1.84 mm/MPa) and about 0.05 inch/psi (184 mm/MPa), and more preferably between about 0.001 inch/psi (3.7 mm/Mpa) and about 0.01 inch/psi (36.8 mm/Mpa), as determined by the standard testing method for material compliance (e.g., as used in the angioplasty industry under conditions of pressure between 0–200 psi (1.3 Mpa) and temperature at 37 C.). Such balloons are also typically capable of reaching a minimum burst pressure of about 180 psi (1.24 Mpa) in a constrained burst test, again using the methodology applied in the angioplasty industry. In turn, such preferred balloon materials will typically have a minimum tensile strength of about 5000 psi (34.5 Mpa), and more preferably of about 7000 psi (48.3 Mpa) or more, as determined using ASTM test method D412. Such a balloon material also preferably exhibits a minimum elongation of about 100%, and more preferably of about 300% or more, as determined using ASTM test method D412.

The durometer of the balloon material should range from 80 shore A to 80 shore D, and more preferably range from 55 shore D to 72 shore D, as determined using ASTM test method D2240. The flexural modulus of the balloon material should preferably range from about 3,000 psi (20.7 Mpa) to about 250,000 psi (1,724 Mpa), and more preferably range from 20,000 psi (140 Mpa) to 150,000 psi (1,034 Mpa), as determined using ASTM testing method D790.

Depending on the desires of the manufacturer and/or surgeon, balloons and biomaterials can be provided to provide any desired physical and/or chemical relationship, including the formation of covalent bonds between the curing polymer and balloon. In order to achieve this, or other purposes, the balloons can be adapted to provide desired interior and/or exterior surface characteristics. The exterior and interior surfaces (of the same or different layers) can be designed or modified to have certain desired characteristics. For example, the exterior surface can be designed or modified to permit or facilitate tissue ingrowth, to allow the implant to be integrated into the host tissue. The interior surface can be designed or modified to enhance the polymer-balloon binding. Examples of surface modifications are chemical grafting and plasma-induced graft polymerization.

Presently preferred balloon components can be made using conventional techniques available in the art, Generally, a mandrel is dip-coated in a polymer solution and dried and cured to form the completed balloon. The process of making the multiple-layered balloon component generally involves more complex techniques. One method of preparing a double-layered balloon component, for instance, generally involves individually preparing the inner and outer layers, and then bonding the two layers together and attaching the balloon to the cannula portion(s) of the device.

The inner layer of a composite balloon can be formed using a thermoplastic polymer (i.e., a polymer or polymer formulation which can be repeatedly heated and melted). A parison (i.e., tube for blow-molding) can be extruded to the desired dimensions and subsequently heated. The parison can be heated either inside of the mold for constrained blowing process, or alternatively, in the absence of a mold, for a free-blowing process. Pressure can then be applied within the heated tubing, typically using a liquid or gas, in order to expand the parison into conformity with the selected dimensions and shape of the mold, or alternatively, to the desired free-blown diameter. The balloon shape and wall thickness are controlled by the selected dimensions of the starting parison and the final blown diameter/shape of the balloon.

The outer layer can be formed using either a thermoplastic polymer or polymer formulation, or alternatively, a thermoset polymer (i.e., a material that can be melted or made flowable only once). The outer layer of the balloon can be formed using a dip-coating process or alternatively, a blow-molding technique.

In the case of the dip-coating technique, a mandrel of the desired configuration (e.g., dimensions and shape) is selected. The mandrel is then placed or dipped into a polymer solution having the desired polymer formulation and viscosity for the molding process. The mandrel is withdrawn from the polymer solution and the polymer-coated mandrel is subjected to a drying and curing step. The drying and curing step is typically performed using a dip-coating machine, which includes a) a mandrel retainer, b) an electronically controlled motor drive for rotating the polymer-coated mandrel to ensure a thorough and uniform distribution of the coating over the mandrel, and c) a heat source, which is typically in the form of a drying gun, heat lamp, and the like). The mandrel is dipped back into solution and dried and cured again. The dipping and drying/curing steps are repeated as often as needed until the desired balloon wall thickness and shape is obtained. After final dip and cure, the finally cured polymer-coated mandrel is placed in an oven or other appropriate heat source is applied so as to obtain a solvent-free, fully cured balloon.

Optionally, in the next step, the shafts of the inner balloon can be necked to a second, smaller diameter shaft composed of the same material using a necking apparatus. Typically, a necking apparatus includes a heat source, dye with a tapered hole (such that when shaft pulled through the dye, a specific diameter results in compliance with the diameter of the hole which is selected according to the desired diameter of the shaft). Generally, necking involves a two-fold result, namely, a decrease in diameter and elongation of shaft material. The shaft is then placed within a metal sleeve in order to maintain the desired diameter.

Preferably, the balloon is then pressurized to desired dimensions and shape using either fluid or gas pressure. The pressure is maintained during the annealing process, or heat-treatment performed under desired temperature and humidity, for a time sufficient to obtain the stable wall thickness and desired geometry of the balloon and shafts. Such heat stabilization prevents the inner, blow-molded balloon material from returning to its original, pre-molded configuration. After the heat treatment, the inner balloon is removed from the metal tubing, and the balloon shafts are cut to the desired length. The delivery cannulas are then bonded to the balloon shaft. Bonding can be accomplished using adhesives or heat-bonding techniques, for example. Next, the outer balloon is positioned over the inner balloon, trimmed to the desired geometry, and bonded to the inner balloon. Bonding can be accomplished using adhesives or heat-bonding techniques, for example. When adhesive is used, for example, the adhesive is placed between the layers, the outer balloon is positioned onto the inner balloon, air is removed from between the layers, and the adhesive is cured to provide adhesion of the two layers.

Alternatively, the outer layer can be bound to the inner layer using heat-bonding techniques. For instance, the outer balloon can be positioned over the inner balloon and the combined assembly then placed into a mold. The layers are then bonded using the appropriate temperature, pressure and time parameters to effectuate bonding between the layers.

Various other balloon molding techniques can be used as well to form multiple-layer balloons for the device of the invention. For instance, co-extrusion, blow molding, and co-blowing techniques can be used.

Co-extrusion techniques such as those described in U.S. Pat. Nos. 5,769,817, 5,797,877 and 5,620,649 can be used as well, the disclosures of which are incorporated herein by reference. In such techniques, a parison is typically co-extruded such that the desired inner layer is contained within the desired outer layer as a result of melt-extrusion process. The two layers are melt-bonded together as a result of the extrusion process. The co-extruded parison can be blow-molded using either a constrained blow-molding technique or a free-blowing technique.

Blow-molding techniques such as those described in International Patent Application No. WO002613A1 and U.S. Pat. No. 5,447,497 can also be used. Co-blowing techniques include those described in U.S. Pat. No. 5,587,125, wherein the parison of the desired inner layer material is formed first, followed by extruding a second parison of the desired outer balloon material. The outer parison is placed over the inner parison, and using appropriate temperature, time, and pressure contained within a mold, the final layered balloon is produced in the desired configuration.

A device of this invention preferably includes first and second lumen, each having proximal and distal ends, with the proximal (i.e., patient) ends of each lumen coupled, or adapted to be coupled, in fluid or gaseous communication with the interior cavity of the balloon. A device of this invention preferably also includes one or more adaptors, preferably including a fluid control valve, associated with the first lumen and adapted to operably and controllably connect and provide fluid communication between the proximal end of the first lumen and a flowable biomaterial delivery apparatus. The device also includes one or more adaptors associated with the second lumen and adapted to operably and controllably affect fluid and/or gas pressure within the balloon in the course of its filling.

The system of the present invention further comprises various cannulas or lumen, e.g., first and second lumen, each having proximal and distal ends, with the proximal ends of each lumen coupled, or adapted to be coupled, in fluid or gaseous communication with the interior cavity of the balloon.

The first and second lumen can be of any relative size, shape or configuration, e.g., they can be provided as separate cannula attached at different sites to the balloon, or they can be provided within and/or upon the same cannula, e.g., as adjacent or coaxial lumen within the cannula sharing one or more portions as a common wall. In a preferred embodiment, the lumen are provided as adjacent cannula.

In an alternative embodiment, the second cannula is attached to the balloon at a location substantially opposite the attachment site of the first cannula in order to optimize the filling of the balloon, and is adapted for insertion through openings in the intervertebral disc.

The adaptor connecting the biomaterial delivery apparatus contains a fluid control valve which controls fluid flow after exiting the apparatus. In a preferred embodiment, a three-way fluid control valve is used which can direct the flow of the biomaterial either straight into the full length of the cannula or, alternatively, divert or redirect the flow aside in order to purge an undesired portion of the biomaterial, the initial portion of which can be inadequately mixed or contain bubbles, for example.

In an additional embodiment, the first cannula further contains an adaptor for attachment of a fluid pressure monitor in communication with the first cannula. The means for controlling fluid pressure inside the cannula and balloon is controlled by adjusting the exit flow of biomaterial through the second cannula. Any mechanism, device, apparatus, or technique which functions to controllably and reversibly restrict fluid flow through a cannula can be used. Examples of suitable fluid pressure control means include, but are not limited to, clamps, valves, hemostats, locking forceps, and the like.

In a preferred embodiment, the mechanism for controlling fluid pressure is readily attachable and removable so as not to obstruct, inhibit or interfere with the insertion of the second cannula through the access portals and openings in the disc. Accordingly, the preferred fluid pressure control means can be attached to the second cannula after the device has been positioned in the body. Alternatively, biomaterial delivery can be controlled by a injection volume control means to deliver certain amount of material which is predetermined based on calculation or measurement of the cavity volume. The one or more biomaterial adaptors, preferably includes a fluid control valve, associated with the first lumen and adapted to operably and controllably connect the proximal end of the first lumen to a biomaterial delivery apparatus.

Lumen and adaptors of suitable for use in the present device can be fabricated from polymeric, stable, compatible materials and used in ways conventional within the industry, e.g., to provide an optimal combination of such properties as compatibility with the biomaterial and tissues, and the ability to be sterilized. In such a preferred embodiment, the system can include a variety of optional features, including an endpoint monitor adapted to provide the surgeon with an indication of a suitable endpoint for biomaterial delivery. In one preferred embodiment, for instance, the endpoint monitor includes a pressure monitor associated with a lumen (preferably the first lumen) of the device, for use in detecting and/or determining a suitable endpoint by determining the distraction pressure brought about by the delivery of biomaterial within the disc space.

The endpoint monitor can be based on parameters other than, or in addition to delivery or distraction pressure, such other parameters being useful either alone or in conjunction with each other. Such endpoint monitors include, for instance, those based on the volume of biomaterial delivered, visualization (e.g., by C arm or interoperative MRI) of the extent of distraction achieved, and the like.

An endpoint monitor can be operably attached between the delivery device and the balloon, and associated with the first lumen of the device, such as a pressure monitor for use in measuring fluid pressure within the lumen and/or balloon. Suitable pressure monitors include any device or system adapted to measure or indicate fluid pressure within a surgical fluid system and adapted for attachment to a surgical system cannula. Examples of suitable pressure monitors include, but are not limited to, those involving a suitable combination of pressure gauge, electronic pressure transducer and/or force transducer components. Such components that can be adapted to permit the accurate and substantially real time measurement of pressure in a remote fluid, by shunting a sample of such fluid, particularly where the fluid is itself undergoing a change in properties in the course of its ongoing cure.

Typically, the pressure monitors used in the system of the invention are integrated into the fluid system, i.e., attached to the first or second cannula. Preferably, the pressure monitor is attached to the first cannula in advance of the balloon such that when the fluid path through the second cannula is adjusted, the pressure as monitored in the first cannula will provide a more comprehensive measurement of the fluid pressure contained within the system. Accordingly, the portion of the cannula upon which die pressure monitor is to be attached contains an adaptor which allows coupling of the monitor onto the cannula.

Optionally, or in addition to the endpoint monitor, the system can include an adaptor for use in shunting the initial or terminal flow of biomaterial between the biomaterial delivery device and the balloon. Such an adapter can be associated with the first lumen of the device, for instance, in order to shunt either an initial portion of the biomaterial and/or terminate the flow of biomaterial from the delivery device to the balloon.

Suitable shunting means includes any device or apparatus adapted for attachment in fluid communication with a surgical cannula and adapted for controllable divergence of the fluid traveling through the cannula. Examples of shunting means include, but are not limited to, reservoirs, three-way valve systems, and the like. Preferably, the shunting means is located proximal to the biomaterial delivery device such that the initial portion of the mixed curable biomaterial can be, temporarily prevented from continuing onward through the device.

A system of this invention, in turn, comprises one or more devices of the types described herein, in combination with:

a) one or more biomaterial sources, at least one of the sources comprising a plurality of parts adapted to be mixed and delivered to the balloon portion of the device in order to be cured in situ within the disc space; and b) one or more corresponding biomaterial delivery devices, each adapted to mix a plurality of biomaterial parts and deliver the curing biomaterial to the balloon portion of the device.

The invention also includes a kit containing the system of the invention and further comprising a biomaterial source and biomaterial delivery apparatus. The kit can further include a cannula insertion guide wire, minimally invasive cannula severing device (such as a co-axial cutting instrument), and devices for facilitating intervertebral disc tissue repair (such as an annular plug as taught by Applicant's U.S. Ser. No. 09/086,848), the disclosure of which is incorporated herein by reference.

A preferred annular plug device, for use in sealing a biological aperture in situ, typically comprises the device comprising a porous, expandable material adapted to be sealably positioned within the biological aperture and to permit natural tissue ingrowth into the device. The material is adapted to be delivered to and positioned within the aperture, in conformity with the dimensions of the aperture, using minimally invasive techniques, and the porous material is adapted to become permanently secured over time, by permitting ingrowth of natural fibrous tissue into some or all of the pores. Ingrowth can be facilitated by incorporating a bioactive agent into the material. Such a device is preferably expandable, such that once positioned the material can swell in order to initially secure the expanded device within the aperture. An examples of a presently preferred material is poly(vinyl alcohol), which can be used provide an annular plug in a configuration selected from the group consisting of cylindrical plugs, tubular forms, and elongated, curved forms. In yet other embodiments, the material can comprise regions of varying chemical and/or physical properties, e.g., wherein the regions are provided in the form of internal and external portions wherein the internal portion is provided in the form of a semi-rigid material used to provide mechanical support. In such an embodiment, either or both portions contain a substance to enable external imaging of the device, e.g., a radio-opaque material suitable to permit imaging by MRI or X-ray. In another preferred embodiment, the plug material can include a bioactive agent is selected from the group consisting of growth factors, angiogenic factors and immune system suppressors, e.g., a growth factor comprising a fibroblast growth factor.

In another aspect, the present invention provides a biomaterial in the form of a curable polyurethane composition comprising a plurality of parts capable of being aseptically processed or sterilized, stably stored, and mixed at the time of use in order to provide a flowable composition and initiate cure, the parts including: (1) a quasi-prepolymer component comprising the reaction product of one or more polyols, and one or more diisocyanates, optionally, one or more hydrophobic additives, and (2) a curative component comprising one or more polyols, one or more chain extenders, one or more catalysts, and optionally, other ingredients such as an antioxidant, hydrophobic additive and dye. Upon mixing, the composition is sufficiently flowable to permit it to be delivered to the body, and there fully cured under physiological conditions. Preferably, the component parts are themselves flowable, or can be rendered flowable, in order to facilitate their mixing and use.

The device described herein is considered novel in its own right, and can be used with any suitable curable biomaterial. In a particularly preferred embodiment, the device is used in combination with a curable polyurethane composition comprising a plurality of parts capable of being aseptically processed or sterilized, stably stored, and mixed at the time of use in order to provide a flowable composition and initiate cure.

The biomaterial used in this invention preferably includes polyurethane prepolymer components that react in situ to form a solid polyurethane ("PU"). The formed PU, in turn, includes both hard and soft segments. The hard segments are typically comprised of stiffer oligourethane units formed from diisocyanate and chain extender, while the soft segments are typically comprised of more flexible polyol units. These two types of segments will generally phase separate to form hard and soft segment domains, since they tend to be incompatible with one another. Those skilled in the relevant art, given the present teaching, will appreciate the manner in which the relative amounts of the hard and soft segments in the formed polyurethane, as well as the degree of phase segregation, can have a significant impact on the final physical and mechanical properties of the polymer. Those skilled in the art will, in turn, appreciate the manner in which such polymer compositions can be manipulated to produce cured and curing polymers with desired combination of properties within the scope of this invention. In a preferred embodiment of this invention, for instance, the hard segment in the formed PU ranges from about 20% to about 70% by weight and more preferably from about 30% to about 50% by weight and the soft segment from about 30% to about 80% and more preferably from about 50% to about 70% by weight, based on the total composition of the formed PU.

The hard segments of the polymer can be formed by a reaction between the diisocyanate or multifunctional isocyanate and chain extender. Some examples of suitable isocyanates for preparation of the hard segment of this invention include aromatic diisocyanates and their polymeric form or mixtures of isomers or combinations thereof, such as toluene diisocyanates, naphthylene diisocyanates, phenylene diisocyanates, xylylene diisocyanates, and diphenylmethane diisocyanates (MDI), and other aromatic polyisocyanates known in the art. Other examples of suitable polyisocyanates for preparation of the hard segment of this invention include aliphatic and cycloaliphatic isocyanates and their polymers or mixtures or combinations thereof, such as cyclohexane diisocyanates, cyclohexyl-bis methylene diisocyanates, isophorone diisocyanates and hexamethylene diisocyanates and other aliphatic polyisocyanates. Combinations of aromatic and aliphatic or arylakyl diisocyanates can also be used.

The isocyanate component can be provided in any suitable form, examples of which include 2,4'-diphenylmethane diisocyanate, 4,4'-diphenylmethane diisocyanate, and mixtures or combinations of these isomers, optionally together with small quantities of 2,2'-diphenylmethane diisocyanate (typical of commercially available diphenylmethane diisocyanates). Other examples include aromatic polyisocyanates and their mixtures or combinations, such as are derived from phosgenation of the condensation product of aniline and formaldehyde. It is suitable to use an isocyanate that has low volatility, such as diphenylmethane diisocyanate, rather than more volatile materials such as toluene diisocyanate. An example of a particularly suitable isocyanate component is the 4,4'-diphenylmethane diisocyanate ("MDI"). Alternatively, it can be provided in liquid form as a combination of 2,2'-, 2,4'- and 4,4'-isomers of MDI. In a preferred embodiment, the isocyanate is MDI and even more preferably 4,4'-diphenylmethane diisocyanate, present at a range from about 20% to about 50% and more preferably from about 25% to about 45% by weight of the total composition of the formed PU.

Some examples of chain extenders for preparation of the hard segment of this invention include, but are not limited, to short chain diols or triols and their mixtures or combinations thereof, such as 1,4-butane diol, 2-methyl-1,3-propane diol, 1,3-propane-diol ethylene glycol, diethylene glycol, glycerol, cyclohexane dimethanol, triethanol amine, and methyldiethanol amine. Other examples of chain extenders for preparation of the hard segment of this invention include, but are not limited to, short chain diamines and their mixtures or combinations thereof, such as dianiline, toluene diamine, cyclohexyl diamine, and other short chain diamines known in the art. In a preferred embodiment, the chain extender is 1,4-butane diol and is present in a range of about 0% to about 20% and more preferably in a range of about 5% to about 15% by weight of the total composition of the formed PU The soft segment consists of urethane terminated polyol moieties, which are formed by a reaction between the polyisocyanate or diisocyanate or polymeric diisocyanate and polyol. Examples of suitable diisocyanates are denoted above. Some examples of polyols for preparation of the soft segment of this invention include but are not limited to polyalkylene oxide ethers derived form the condensation of alkylene oxides (e.g. ethylene oxide, propylene oxide, and blends thereof), as well as tetrahyrofuran based polytetramethylene ether glycols, polycaprolactone diols, polycarbonate diols and polyester diols and combinations thereof. In a preferred embodiment, the polyols are polytetrahydrofuran polyols ("PTHF"), also known as polytetramethylene oxide ("PTMO") or polytetramethylene ether glycols ("PTMEG") present in a range about 30% to about 90% by weight of the total formed urethane composition. Even more preferably, the use of two or more of PTMO diols with different molecular weights selected from the commercially available group consisting of 250, 650, 1000, 1400, 1800, 2000 and 2900 and present in a range of about 50% to about 80% by weight of the total formed urethane composition.

Two or more PTMO diols of different molecular weight can be used as a blend or separately, and in an independent fashion as between the different parts of the two part system. The solidification temperature(s) of PTMO diols is generally proportional to their molecular weights. The compatibility of the PTMO diols with such chain extenders as 1,4 butanediol is generally in the reverse proportion to molecular weight of the diol(s). Therefore the incorporation of the low molecular weight PTMO diols in the "curative" (part B) component, and higher molecular weight PTMO diols in the prepolymer (part A) component, can provide a two-part system that can be used at relatively low temperature. In turn, good compatibility of the low molecular weight PTMO diols with such chain extenders as 1,4 butanediol permits the preparation of two part systems with higher (prepolymer to curative) volume ratio. Amine terminated polyethers and/or polycarbonate-based diols can also be used for building of the soft segment.

The PU can be chemically crosslinked, e.g., by the addition of multifunctional or branched OH-terminated crosslinking agents or chain extenders, or multifunctional isocyanates. Some examples of suitable crosslinking agents include, but are not limited to, trimethylol propane ("TMP"), glycerol, hydroxyl terminated polybutadienes, hydrogenated polybutadienes, trimer alcohols, Castor oil polyethyleneoxide (PEO), polypropyleneoxide (PPO) and PEO-PPO triols. In a preferred embodiment, TMP is used as the crosslinking agent and is present from about 0% to about 1% and more preferably from about 0.05% to about 0.5% by weight of the total composition of the formed PU.

This chemical crosslinking augments the physical or "virtual" crosslinking of the polymer by hard segment domains that are in the glassy state at the temperature of the application. The optimal level of chemical cross-linking improves the compression set of the material, reduces the amount of the extractable components, and improves the biodurability of the PU. This can be particularly useful in relatively soft polyurethanes, such as those suitable for the repair of damaged cartilage. Reinforcement by virtual cross-links alone may not generate sufficient strength for in vivo performance in certain applications. Additional cross-linking from the soft segment, potentially generated by the use of higher functional polyols can be used to provide stiffer and less elastomeric materials. In this manner a balancing of hard and soft segments, and their relative contributions to overall properties can be achieved.

Additionally, a polymer system of the present invention preferably contains at least one or more, biocompatible catalysts that can assist in controlling the curing process, including the following periods: (1) the induction period, (2) the setting period, and finally, (3) the final cure of the biomaterial. Together these three periods, including their absolute and relative lengths, and the rate of acceleration or cure within each period, determines the cure kinetics or profile for the composition. Some examples of suitable catalysts for preparation of the formed PU of this invention include, but are not limited to, tin and tertiary amine compounds or combinations thereof such as dibutyl tin dilaurate, and tin or mixed tin catalysts including those available under the tradenames "Cotin 222", "Formrez UL-22" (Witco), "DABCO" (a triethylene diamine), stannous octanoate, trimethyl amine, and triethyl amine. In a preferred embodiment, the catalyst is Formrez UL-22 (Witco) and is used at a range from about 0% to about 1% and more preferably from 0.01 to about 0.1% by weight of the total composition of the PU.

The polyurethanes of this invention can be formed by the reaction of two parts. Part I of which (alternatively referred to as Part A) includes a di- or multifunctional isocyanate or quasi-prepolymer which is the reaction product of one or more OH-terminated components, and one or more isocyanates. Part II of the polyurethane (alternatively referred to as Part B herein) is a curative component that includes of one or more chain extenders and one or more polyols, and one or more catalysts, and other additives such as antioxidants and dyes. For a suitable formed PU, the stoichiometry between Parts I (quasi-prepolymer) and II (curative component), expressed in terms of NCO:OH molar ratio of the isocyanate terminated pre-polymer (Part I) and the curative component (Part II) is preferably within the range of about 0.8 to 1.0 to 1.2 to 1.0, and more preferably from about 0.9 to 1 to about 1.1 to 1.0.

The schoichiometry (i.e., ratio of NCO to OH) of a polymer system can affect the cured properties, such as leachables, tear resistance and wear resistance. Applicants have found that a polymer with NCO to OH ratio less than about 1 has better tear resistance and wear resistance, which are both important to the disc prosthesis application, than the polymer with NCO to OH ratio 1 or more. For improved wear and tear resistance, it is preferable to have the NCO to OH ratio between about 0.95 and about 1.

The following table summarizes the overall composition ranges and the preferred polyurethane composition of the current invention (by weight % based on the weight of the final polymer composition):

|  | Overall Range | Preferred |
|---|---|---|
| Hard Segments | 20–70 | 30–50 |
| Soft Segments | 30–80 | 50–70 |
| Isocyanates | 20–50 | 25–45 |
| Polyols | 30–90 | 50–80 |
| Extenders - linear | 0–20 | 5–15 |
| Extenders - branched | 0–1 | 0.05–0.5 |
| Catalysts | 0–1 | 0.01–0.1 |
| NCO:OH | 0.8 to 1.2:1 | 0.9 to 1.1:1 |

Optionally, a reactive polymer additive can be included at a concentration of between about 0% and about 25% by weight, and is selected from the group consisting of hydroxyl- or amine-terminated compounds selected from the group consisting of polybutadiene, polyisoprene, polyisobutylene, silicones, polyethylenepropylenediene, copolymers of butadiene with acryolnitrile, copolymers of butadiene with styrene, copolymers of isoprene with acrylonitrile, copolymers of isoprene with styrene, and mixtures of the above. In such an embodiment, for instance, the additive can comprise hydroxyl-terminated polybutadiene, present at a concentration of between about 5% and about 30%, by weight, and preferably between about 5% and about 20% by weight.

As applied to intervertebral disc repair, the inclusion of a "reactive hydrophobic additive" in the prepolymer, while was previously described and is presently preferred by Applicants in formulations for joints other than the disc, is not presently preferred (though remains optional) for use in the disc. When present, such an additive can provide several desirable features, both in the formulation and use of the prepolymer itself, as well as in the mixed composition. These features include an improved combination of such properties as moisture cure characteristics, cross-linking, viscosity, compression fatigue, and stability.

The composition of the current invention provides improved properties, including an improved combination of such properties as hardness, strength and/or cure characteristics, as compared to compositions previously known., Applicants have discovered that such improvement can be achieved without detrimental effect on other desired properties, including those that arise (a) prior to delivery, (b) in the course of delivery (including whatever mixing, curing, and/or shaping that may occur), and finally, (c) following cure and in the course of extended use in the body.

When cured, suitable materials can be homogeneous, providing the same physico-chemical properties throughout, or they can be heterogeneous and exhibit varying features or properties. An example of a heterogeneous composition, e.g., for use as an intervertebral disc replacement, is a composition that mimics the natural disc by providing a more rigid outer envelope (akin to the annulus) and an more liquid interior core (akin to the nucleus). Such heterogeneous compositions can be prepared by the use of a single composition, e.g., by employing varying states of cure and/or by the use of a plurality of compositions, including varying compositions and/or ratios of the same ingredients used to form the composition.

Suitable compositions for use in the present invention are those polymeric materials that provide an optimal combination of properties relating to their manufacture, application, and in vivo use. In the uncured state, such properties include component miscibility or compatibility, processability, and the ability to be adequately sterilized or aseptically processed and stored. In the course of applying such compositions, suitable materials exhibit an optimal combination of such properties as flowability, moldability, and in vivo curability. In the cured state, suitable compositions exhibit an optimal combination of such properties as strength (e.g., tensile and compressive), modulus, biocompatibility and biostability.

When cured, the compositions demonstrate an optimal combination of properties, particularly in terms of their conformational stability and retention of physical shape, dissolution stability, biocompatibility, and physical performance, as well as physical properties such as density and surface roughness, and mechanical properties such as load-bearing strength, tensile strength, shear strength, shear fatigue resistance, impact absorption, wear resistance, and surface abrasion resistance. Such performance can be evaluated using procedures commonly accepted for the evaluation of natural tissue and joints, as well as the evaluation of materials and polymers in general. In particular, a preferred composition, in its cured form, exhibits mechanical properties that approximate or exceed those of the natural tissue it is intended to provide or replace.

At uncured stage, preferred components of compositions, and compositions themselves, should be miscible, compatible and stable under conditions used for sterilization and during storage and in the course of delivery. They are also capable of flowing through a delivery cannula to an in vivo location, and being cured in situ, as by chemical catalysis, by exposure to an energy source such as ultraviolet light, or by chemical reaction producing exotherm. Thereafter the cured composition is suitably amenable to shaping and contouring, by the use of conventional or custom designed arthroscopic tools or instruments. Over the course of its use in the body the cured, contoured composition exhibits physiological, physical-chemical and mechanical properties suitable for use in extended in vivo applications.

To achieve these desirable uncured and delivery properties, a "polymer system", as used herein refers to the component or components used to prepare a polymeric composition of the present invention. In a preferred embodiment, a polymer system comprises the components necessary to form two parts: Part I being an NCO terminated pre-polymer (optionally referred to as an "isocyanate quasi-polymer"). The quasi-polymer of Part I typically includes a polyol component, optionally in combination with a hydrophobic additive component, and an excess of an isocyanate component. Part II of the two component system can include one long-chain polyols, chain extenders and/or cross-linkers, together with other ingredients (e.g., catalysts, stabilizers, placticizers, antioxidants, dyes and the like). Such adjuvants or ingredients can be added to or combined with any other component thereof either prior to or at the time of mixing, delivery, and/or curing.

In a particularly preferred embodiment, a polymer system of this invention is provided as a plurality of component parts and employs one or more catalysts. The component parts, including catalyst, can be mixed to initiate cure, and then delivered, set and fully cured under conditions (e.g., time and exotherm) sufficient for its desired purpose. Upon the completion of cure, the resultant composition provides an optimal combination of properties for use in repairing or replacing injured or damaged tissue. In a particularly preferred embodiment, the formulation provides an optimal combination of such properties as compatibility and stability of the biomaterial parts, in situ cure capability and characteristics (e.g., extractable levels, biocompatibility, thermal/mechanical properties), mechanical properties (e.g., tensile, tear and fatigue properties), and biostability.

The volume ratio of the parts can also be used to improve and affect the uncured and curing properties Compositions having two or more parts, are preferred. Where two parts are used, the relative volumes can range, for instance, from 1:10 to 10:1 (quasi-prepolymer to curative components, based on volume). A presently preferred range is between 2:1 and 1:2. As those skilled in the art will appreciate, given the present description, the optimal volume ratio is largely determined by the compatibility and the stability of part A and B.

In choosing an optimal volume ratio for a given formulation, the following things have be taken into consideration:

The viscosity of the reactive parts in this temperature range must be such to provide an acceptable degree of mixing and injection flow rate without mechanical failure of any component of the delivery system including cartridge, static mixer, gun and other components. Preferably, the biomaterial is sufficiently flowable to permit it to be delivered (e.g., injected) into the balloon). While such a material can be as thick as the bone cement paste, the preferred viscosity is less than 100 Pa s and the most preferred viscosity is less than 10 Pa s.

The composition of both reactive parts must be such that these parts are homogeneous and phase stable in the temperature range of the application.

The max temperature of the reaction exotherm is proportional to the concentration of the reactive groups in the mixed polymer. A high concentration of the reactive groups might evolve too high reaction exothermal energy and therefore cause thermal damage to the surrounding tissues. The preferable implant-tissue interface temperature is below 80 C., and more preferable below 70 C.

The reactive parts must stay liquid during mixing. The complete or partial solidification of the reactive part when it comes into contact with another reactive part or any component of the delivery system or during mixing is unacceptable.

The certain volume ratio of the components can be achieved by different ways such as use of the dual-compartment cartridges with constant volume ratio or by using the injectors with delivery rates independently variable for each component.

Many mixing devices and methods have been used for two-part biomaterials, such as bone cement and tissue sealant, used in operating rooms. Many mechanical mixing devices, such as the ones disclosed in U.S. Pat. Nos. 5,797,679 and 6,042,262, have been used for bone cement mixing. These mechanical mixing devices, however, can take a long time to get thorough mixing and can be difficult to operate in sterile field, especially for the two-component biomaterials with short cure time. On the other hand, some prior art two-part polyurethanes have a gel time about 30 minutes. Without a proper seal method to seal off the polymer delivery catheter, a cure time of 30 minutes is too long for operating room use.

Static mixers and manual dispenser guns are commonly used for tissue sealant and other two-component biomaterial mixing and delivery, such as disclosed in U.S. Pat. No. 6,079,868. While these mixing and delivery devices appear to be suitable to mix the two components and cure the polymer for the two-component polyurethane, a closer examination using an organic solvent to swell the cured polymer revealed that a standard Kenics® static mixers (available from Chemineer, Inc. of North Andover, Mass.) with 32 mixing elements and a manual dispensing gun did not provide adequate mixing for the two-component polyurethane.

It is important that the two parts of polyurethane prepolymer are mixed quickly and completely in the operating room in a sterile fashion. Biomaterials with induction times of less than 60 seconds and cure times less than 5 minutes require a different mixing and delivery device. For two-part polyurethane biomaterials, due to the sensitivity of NCO to OH ratio to the final properties of the cured polymer, there are several features that are important to the final properties of the in situ cured polymer. Three factors appear to have an impact on the in situ curable polyurethane mixing and delivery.

1. Number of mixing element. For most two-component biomaterials, 7–32 mixing elements in a static mixer are sufficient to provide adequate mixing (see Brandywine Associates mixer catalog at www.staticmixerdispenser.com). When a 32 mixing elements mixer is used with certain two-component polyurethane, it was found the mixing was not adequate. Data showed that a static mixer with at least about 45 to about 65 mixing elements is preferred, and more preferably about 50 to about 60 mixing elements. It should be noted that more mixing elements is not necessarily better for mixing and delivery of all polymers. A mixer with too many mixing elements can lead to high pressure drop during the polymer delivery.

2. Purge of the initial volume from the static mixer. Mixture of the initial portion in a static mixer often does not lead to a well cured polymer. The causes of this could be poor mixing or the mixture out of the right stoichiometry. It is preferred to purge off an initial volume of biomaterial equal to about 1 times to about 4 times, and preferably about 2 times, the volume of the static mixer. See generally U.S. Pat. No. 6,079,868. In one embodiment, purging is achieved using a manual 3-way stop-cock or an automatic in-line purge device.

3. The effect of polymer flow during delivery using a static mixer. For most two-component tissue sealants, a manual dispenser, such as the DMA 51 Manual Dispensing Gun and Plungers (available from Brandywine Associates), is used to dispense the two-component materials from the cartridge when using a static mixer for mixing. It normally takes several strokes of the manual dispensing device in order to deliver enough material to fill the mixer volume, to purge the initial portion, and for the final application. In some circumstances, the use of a manual dispenser results in a final polymer that is not adequately mixed. The lack of mixing is believed to be due to the pulsating, irregular and/or discontinuous flow from the manual dispenser. It is also possible that differences in viscosity of the two parts of the polymer and/or stored energy in the static mixing tube or other delivery hardware contribute to the irregular flow. Consequently, a substantially constant flow rate and/or a substantially continuous flow of polymer is preferred for optimum mixing for polyurethane.

The compatibility of a polymer system can also be achieved by having more than the traditional two parts, e.g., three or more parts, and mixing them all together prior to polymer application. By storing the incompatible components in different cartridges, it often can minimize the concern of component incompatibility. One example of a three-part polymer system is to separate the polyol and chain extender in part B of a two-part system.

In a preferred embodiment for the quasi-prepolymer of Part I, the diisocyanate is 4,4'-diphenylmethane diisocyanate (MDI) and is present in large excess after the prepolymer is formed. Total isocyanate ranges from 10%–100% and more preferably from 40%–70% by weight of Part I. The term "quasi-prepolymer", as used herein with respect to the present invention will refer to a diisocyanate terminated prepolymer containing some excessive free diisocyanate.

Compatibility of the composition can also be affected (and improved) in other ways as well, e.g., by pre-heating the components prior to polymer application. To enhance the homogeneity of the components, the components of a preferred composition of this invention are preferably preheated before mixing and delivery, e.g., by heating to about 60–80 C. for about 2 to about 6 hours prior to use. Preferably, the composition parts are cooled back to about 35 to 37 C. before use.

Similarly, in situ curability can also be optimized, while maintaining the desired balance of biocompatibility and mechanical properties. Applicants have used several different ways to optimize the in situ curability. One is to add hydrophobic additives, such as hydrophobic polyols described herein. Alternative approaches include the use of high catalyst levels, the addition of crosslinking agent (e.g., TMP), and/or the use of more reactive ingredients, such as aromatic diisocyanate instead of aliphatic diisocyanate, and 4,4'-MDI instead of 4,2'- and 2,2'-MDI.

In situ curability is largely dependent on the reaction rate, which can be measured by induction time and cure time. In general, fast cure (short induction time) will improve in situ curability by providing more complete polymerization, less leachable components, and better mechanical properties (e.g., less "cold layer" formed due to the cold surface of the implant). However, induction time should also be balanced with adequate working time needed for polymer injection and distraction. Particularly for use in the disc, Applicants have determined that shorter induction times tend to provide improved polymer properties. For such uses, the induction time can be between about 5 and about 60 seconds, for instance, preferably between about 5 and about 30 seconds, and most preferably between about 5 and about 15 seconds. By comparison, the total cure time for such compositions can be on the order of 5 minutes or less, preferably on the order of 3 minutes or less, and most preferably on the order of one minute or less.

In addition to the static mechanical properties claimed before (tensile strength, hardness), a preferred biomaterial also provides an optimal combination of dynamic fatigue properties as well. One of the simple way to state the fatigue requirement is to subject the device to cyclic load between the physiological load of 0.5 to 1.0 Mpa for at least 10 million cycles, preferred 40 million cycles.

A cured biomaterial of this invention preferably exhibits a compression modulus of between about 0.1 MPa and about 50 MPa, and more preferably between about 1 MPa and about 25 MPa, when measured using ASTM method D575A at a physiological strain range between 3–20%. Compositions having a compression modulus considerably below these levels will tend to either bulge or extrude from annular defects that may exist or appear, while those having a modulus considerably above these levels will tend to be too hard and cause stress shielding and abnormal high contact stress on the endplate.

The invention provides a method of preparing and a method of using such a system. In a further aspect, the invention provides a cured composition (optionally within a mold apparatus), for use in apposition to a joint surface, as well as the combination of such a joint surface with a cured composition (optionally within a mold apparatus) in apposition thereto.

The present invention provides an apparatus and method for forming a prosthesis, in situ, the method, in a preferred embodiment, comprising the steps of:

a) providing an implantable mold apparatus comprising a cavity adapted to receive and contain a flowable biomaterial and a conduit adapted to connect the cavity to a source of curable, flowable biomaterial, b) inserting the mold, preferably by minimally invasive means, to a desired site within the body, c) delivering biomaterial to the mold in order to fill the cavity to a desired extent, d) permitting the biomaterial to cure to a desired extent, and e) employing the molded biomaterial in situ as a prosthetic device.

The apparatus, in turn, provides an implantable mold apparatus comprising an expandable cavity adapted to receive and contain a flowable biomaterial in a geometry, configuration and/or position optimal for the intended purpose, and a conduit adapted to connect the cavity to a source of curable, flowable biomaterial. The conduit is preferably removable from the filled cavity, e.g., by cutting it at or near the point where it joins the cavity. Optionally, and preferably, the apparatus further includes means for providing positive or negative air pressure within or to the biomaterial cavity, in order to facilitate the delivery of biomaterial and/or to affect the final shape of the cured mold.

The apparatus and method can be used for a variety of applications, including for instance, to provide a balloon-like mold for use preparing a solid or intact prosthesis, e.g., for use in articulating joint repair or replacement and intervertebral disc repair. Alternatively, the method can be used to provide a hollow mold, such as a sleeve-like tubular mold for use in preparing implanted passageways, e.g., in the form of catheters, such as stents, shunts, or grafts.

In yet another aspect, the invention provides a mold apparatus useful for performing a method of the invention, e.g., in the form of an inflatable balloon or tubular mold, preferably in combination with the conduit used to deliver biomaterial. Along these lines, the invention further provides a system useful at the time of surgery to prepare an implanted prosthesis in vivo, the system comprising a mold apparatus (e.g., cavity and conduit) in combination with a supply of curable biomaterial, and optionally, with a source of positive and/or negative air pressure.

The present invention provides a method and system for the repair of natural tissue that involve the delivery of a biomaterial composition using minimally invasive means, the composition being curable in situ in order to provide a permanent replacement for natural tissue. Optionally, and preferably, the biomaterial is delivered to a mold apparatus that is positioned by minimally invasive means and filled with biomaterial composition, which is then cured in order to retain the mold and cured composition in situ.

As used herein the following words and terms shall have the meanings ascribed below:

"repair" will generally refer to the use of a composition to augment, replace or provide some or all of the structure or function of natural tissue in vivo, for instance, to provide an implant such as a nucleus, or to repair (e.g., reconstruct or replace) degenerative disc. Repair can take any suitable form, e.g., from patching the tissue to replacing it in its entirety, preferably in a manner that reconstructs its natural or other desired dimensions;

"cure" and inflections thereof, will generally refer to any chemical transformation (e.g., reacting or cross-linking), physical transformation (e.g., hardening or setting), and/or mechanical transformation (e.g., drying or evaporating) that allows a composition to change or progress from a first physical state or form (generally liquid or flowable) that allows it to be delivered to the site, into a more permanent second physical state or form (generally solid) for final use in vivo. When used with regard to the method of the invention, for instance, "curable" can refer to uncured composition, having the potential to be cured in vivo (as by catalysis or the application of a suitable energy source), as well as to a composition in the process of curing (e.g., a composition formed at the time of delivery by the concurrent mixing of a plurality of composition components). As further described herein, in selected embodiments the cure of a composition can generally be considered to include three stages, including (a) the onset of gelation, (b) a period in which gelation occurs and the composition becomes sufficiently tack-free to permit shaping, and (c) complete cure to the point where the composition has been finally shaped for its intended use.

"minimally invasive means" refers to surgical means, such as microsurgical or endoscopic or arthroscopic surgical means, that can be accomplished with minimal disruption of the pertinent musculature, for instance, without the need for open access to the tissue injury site or through minimal incisions (e.g., incisions of less than about 4 cm and preferably less than about 2 cm). Such surgical means are typically accomplished by the use of visualization such as fiberoptic or microscopic visualization, and provide a postoperative recovery time that is substantially less than the recovery time that accompanies the corresponding open surgical approach;

"mold" will generally refer to the portion or portions of an apparatus of the invention used to receive, constrain, shape and/or retain a flowable biomaterial in the course of delivering and curing the biomaterial in situ. A mold may include or rely upon natural tissues (such as the annular shell of an intervertebral disc) for at least a portion of its structure, conformation or function. The mold, in turn, is responsible, at least in part, for determining the position and final dimensions of the cured prosthetic implant. As such, its dimensions and other physical characteristics can be predetermined to provide an optimal combination of such properties as the ability to be delivered to a site using minimally invasive means, filled with biomaterial, prevent moisture contact, and optionally, then remain in place as or at the interface between cured biomaterial and natural tissue. In a particularly preferred embodiment the mold material can itself become integral to the body of the cured biomaterial.

As described herein, a mold apparatus will generally include both a cavity for the receipt of biomaterial and a conduit for the delivery of biomaterial to that cavity. Some or all of the material used to form the cavity will generally be retained in situ, in combination with the cured biomaterial, while some or all of the conduit will generally be removed upon completion of the method. An implanted prosthesis, in turn, can be used to replace, provide, or supplement the structure or function of natural tissue in vivo. The prosthesis can take any suitable form, e.g., including patching, repairing or replacing tissue (such as knee or intervertebral disc), supporting existing tissue (as by a stent, for instance), or creating new material having a tissue like function (as by a shunt).

The word "biomaterial" will be used interchangeably with the word "composition", when used in the context of the present invention, and will generally refer to a material that is capable of being introduced to the site of a joint and cured to provide desired physical-chemical properties in vivo. In a preferred embodiment the term will refer to a material that is capable of being introduced to a site within the body using minimally invasive means, and cured or otherwise modified in order to cause it to be retained in a desired position and configuration. Generally such biomaterials are flowable in their uncured form, meaning they are of sufficient viscosity to allow their delivery through a cannula of on the order of about 1 mm to about 6 mm inner diameter, and preferably of about 2 mm to about 3 mm inner diameter. Such biomaterials are also curable, meaning that they can be cured or otherwise modified, in situ, at the tissue site, in order to undergo a phase or chemical change sufficient to retain a desired position and configuration.

In one preferred embodiment, the method of the invention is used in the course of intervertebral discectomy. In an amphiarthroidal joint such as the lumbar joint of the back, the vertebra are separated by an intervertebral disc formed of cartilage. Applicant's copending PCT Application No. PCT/US97/00457 (the entirety of which is incorporated herein by reference), inter alia, describes a method for repairing an intervertebral disc that comprises the steps of:

a) using any suitable surgical techniques to perform a discectomy while preserving annular shell, b) providing one or more curable biomaterials to the interior of the annular shell, and c) curing the biomaterials in order to provide a replacement disc.

As can be seen, the annular shell can itself serve as a suitable mold for the delivery and curing of biomaterial. Optionally, the interior surface of the annular shell can be treated or covered with a suitable material in order to enhance its integrity and use as a mold. Preferably, one or more inflatable devices, such as the balloons described herein, can be used to provide molds for the delivery of biomaterials. More preferably, the same inflatable devices used to distract the joint space can further function as molds for the delivery and curing of biomaterial.

Optionally, a balloon can be provided that fills less than the entire volume of the annular shell. In such an embodiment, the balloon can be, for instance, in the shape of a cylinder. Such a balloon can be provided such that its ends can be positioned to contact the opposing vertebral bodies, and its walls will provide sufficient strength to cause distraction of the space upon inflation.

Thereafter, a first biomaterial is delivered to perimeter of the annular space, i.e., the space between the annular material and the balloon, and there cured. The biomaterial is delivered using suitable means, and under conditions suitable to ensure that it will not extrude through tears in the annulus. Optionally, the balloon can be gradually deflated as additional biomaterial is inserted into the space.

With the outer biomaterial cured in place, the balloon can be removed and an additional biomaterial, of either the same or a different type, can be delivered and cured in whatever remaining space was previously occupied by the balloon. A second cannula can be used to deliver a second biomaterial, preferably one that cures to provide a more flexible region that more closely approximates the physical characteristics of the original nucleus. This method provides the option to reconstruct the disc in a manner that more closely approximates the overall physical characteristics and relationship of the original annulus and nucleus.

A two step approach, as described above, is preferred for a number of reasons. It provides the means for distracting the joint, while at the same time facilitating the preparation of a final reconstructed annulus having two or more regions. The different regions, i.e., a rigid outer shell in combination with a more liquid interior, can provide a function that mimics that of the native disc. In addition to a two step approach, however, an implant having a plurality of regions, can be provided by other means as well. For instance, such an implant can be provided by the delivery of a single biomaterial that is cured to a greater or differing extent in its outermost, as compared to innermost, regions. An implant having a plurality of regions, or even a continuum of properties, is particularly preferred.

In a preferred embodiment, the distraction of the disc space is accomplished by the use of suitable distraction means, such as an inflatable balloon or bladder. The balloon can be delivered in deflated form to the interior of the annulus and there inflated, as by the delivery of biomaterial, in order to distract the disc space and retain the biomaterial.

Figure 5:
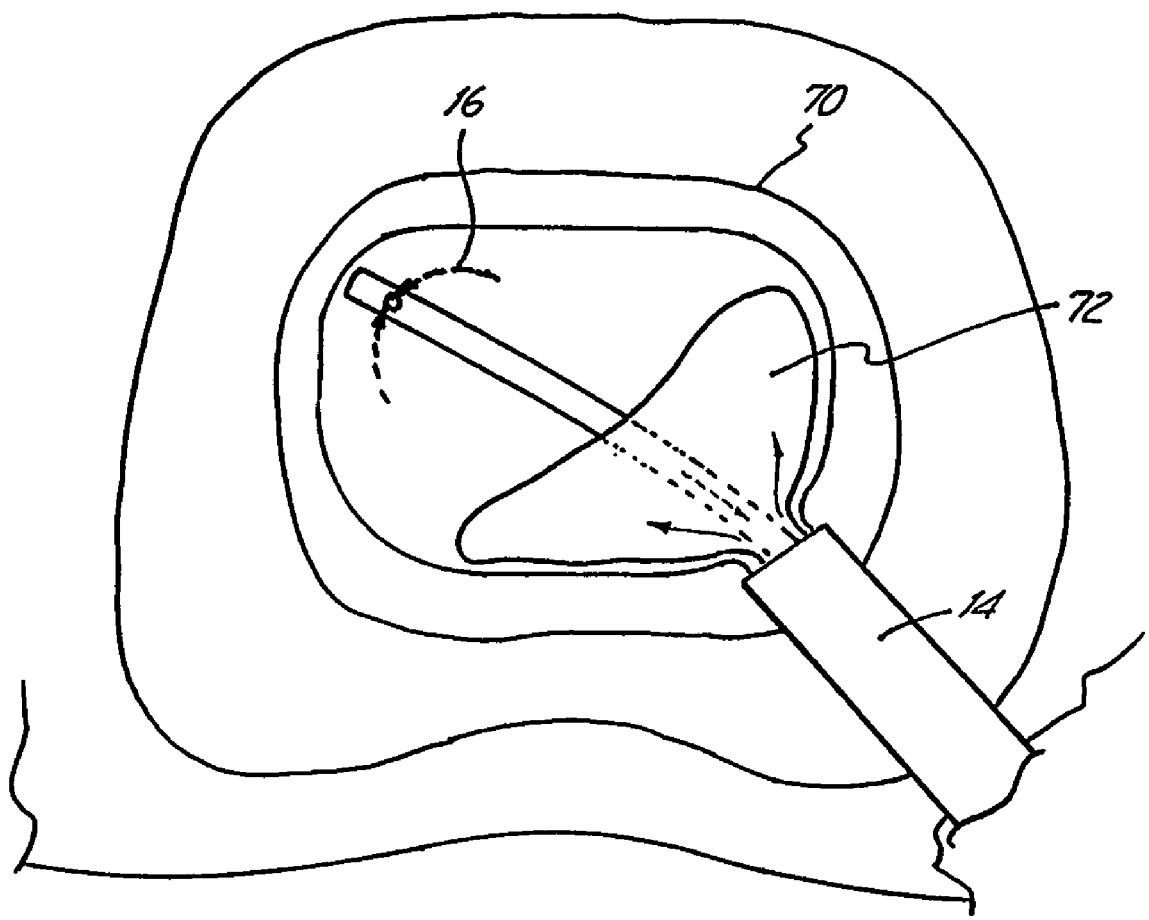
FIG. 5 shows the balloon of FIG. 1 positioned within the disc space and in the course of filling with biomaterial.

The use of a preferred mold apparatus will be described with reference to FIG. 5, which shows the balloon portion (12) in place, with sheath (26) retracted, within an annular shell (70). A curable biomaterial (72) is delivered into the balloon at the same time that air is withdrawn from the balloon through vent holes (22) of air passageway (18). In use, and with the balloon positioned within the sheath, the apparatus can be inserted into the body through minimally invasive means in order to position the proximal end at the site of intended use, e.g., within the disc space. Once positioned, the sheath can be withdrawn in order to release the balloon. Optionally, air or other suitable gas can be delivered to the balloon through the air passageway in order to position the balloon and/or distract the joint. Thereafter, the valve can be opened to begin the flow of curable biomaterial. As biomaterial enters the balloon, gas in the balloon can be vented through air passageway by drawing a slight vacuum on the distal end of the passageway, as by the use of a syringe or other suitable vacuum source. The biomaterial continues to fill the balloon, which in turn serves to distract (or assist in distracting) the space, until desired distraction pressure or dimensions are obtained, whereupon the flow of biomaterial is stopped, the biomaterial is allowed to continue to fully cure (harden), and the balloon severed from the conduit.

The method and apparatus of the invention can also be used to repair other joints, including diarthroidal and amphiarthroidal joints. Examples of suitable diarthroidal joints include the ginglymus (a hinge joint, as in the interphalangeal joints and the joint between the humerus and the ulna); throchoides (a pivot joint, as in superior radio-ulnar articulation and atlanto-axial joint); condyloid (ovoid head with elliptical cavity, as in the wrist joint); reciprocal reception (saddle joint formed of convex and concave surfaces, as in the carpo-metacarpal joint of the thumb); enarthrosis (ball and socket joint, as in the hip and shoulder joints) and arthrodia (gliding joint, as in the carpal and tarsal articulations).

Another aspect of the invention involves a method of providing an intervertebral disc prosthesis, in a particularly preferred embodiment, the method comprising the steps of preparing and accessing the disc. Gaining access to the intervertebral disc, optionally in a minimally invasive fashion and creating a space by removing damaged or diseased tissue from disc, e.g., by performing a microdiscectomy or discectomy/annulotomy.

The method of the invention can be performed using either open or arthroscopic surgical techniques. When arthroscopic surgical techniques are used, access portals can be created to provide access to the intervertebral disc while avoiding damage to the surrounding tissue. A biportal access system is preferred, since such a system allows for better maneuverability of the first and second cannula throughout the procedure. A number of approaches to accessing the disc are possible, including but not limited to, posterio-lateral, retroperitoneal, anterior laproscopic (or open), and posterior open approaches. When open approach is used, a monoportal access system is preferred.

Once the intervertebral disc has been accessed, an access opening must be created through the annulus to access the interior portion of disc and the nucleus. The opening through the annulus can be created by way of a partial annulotomy or dilation techniques. Whichever technique is used, it is desirable to leave as much annular tissue intact as possible.

Damaged or diseased tissue can be removed from the nucleus using any instrument or technique adapted to remove the tissue from the interior portion of the intervertebral disc while minimizing damage or trauma to the surrounding disc tissue. Either manual or motorized/automated instruments can be used to remove the nuclear tissue. Examples of suitable instruments and techniques include, but are not limited to, rongeurs (preferably steerable rongeurs) the Nuceotome™ device available from Surgical Dynamics, CT), motorized shavers (preferably steerable shavers such as the MDS™ microdebrider system available front Endius, Plainsville, Mass.), chemonucleolysis, laser techniques, and the like.

Removal of the nuclear tissue can be partial or total, depending upon the patient's condition. The extent of disc tissue removed must be at least sufficient to accommodate the prosthesis to be implanted with the device. Accordingly, the nuclear portion of the disc is removed to form a cavity or chamber having the dimensions to sufficiently accommodate the final cured form of the prosthesis in concordance with the prosthetic dimensions (i.e., height, width, circumference) as are necessary to restore the patient's intervertebral requirements. The amount of nuclear tissue removed will vary according the patient's condition, disc size, and instruments used. Typically, the amount removed is within the range of from about 2 grams to about 8 grams.

Providing a system of the present invention, including a device comprising an expandable balloon portion and a biomaterial delivery device and biomaterial source and inserting the expandable balloon component of the device into the created disc space (e.g., into the nuclear portion of the disc), for instance, by the use of an introducing cannula that contains the balloon in a compact form, and that provides a proximal end adapted to be secured to tissue within the disc space.

Introducing and positioning the balloon within the space, e.g., by retracting the introducing cannula and/or extending the compacted balloon from the introducer into the space, preferably in a manner and under conditions suitable to permit the balloon to conform itself, at least in part, to the available space.

Next, the device of the invention is provided and inserted through the disc so as to position the balloon portion of the device within the nuclear cavity inside the disc, Additional surgical instruments and techniques can be used to facilitate the insertion and placement of the device into the appropriate position. For instance, a guide wire can initially be inserted through the access portals and annular openings through the disc, and the cannula and balloon portions of the device slid over the guide wire until the balloon is positioned within the disc. Suitable guide wire devices include steerable angioplasty guide wire available from Cook Inc. (Bloomington, Ind.). The distal end of the second cannula can be truncated so as to allow for unobstructed insertion through the body.

The proper positioning of the balloon within the disc can be verified using currently available techniques, such as fluoroscopy, intraoperative CT scanning, x-ray, and the like. In an additional embodiment, positioning markings or other externally detectable indicia can be used to aid in verifying the positioning of the device.

Biomaterial is delivered by a) drawing a vacuum on the balloon, with fluid communication to the biomaterial in a closed position, b) mixing a plurality of biomaterial parts in order to initiate cure, and filling the balloon with the mixed and curing, yet flowable, biomaterial, preferably after shunting an initial portion of the mixed biomaterial, and c) permitting the biomaterial to expand and fully cure within the balloon to form a prosthesis, wherein the filling and expansion of the balloon and the curing of the biomaterial are performed by controlling the fluid pressure of the biomaterial within the device throughout the procedure, optionally and preferably within a time period and with a pressure sufficient, in whole or in part, to achieve and/or maintain intervertebral distraction.

Prior to delivering the flowable biomaterial to the device, the pressure monitor can be attached to the cannula by way of an adaptor or attachment means for coupling the monitor to the cannula. Prior to filling the balloon, the uncured, flowable biomaterial is mixed and delivered to the proximal portion of the first cannula, at which point the initial portion of the mixed biomaterial is shunted to dispose of inadequately mixed or otherwise undesirable biomaterial prior to continuing throughout the device. Accordingly, the flow path of the initial biomaterial is diverted using a shunting means as described herein.

In one embodiment, a three-way valve is adjusted so as to divert the flow into a shunt or reservoir. Once the less preferred biomaterial has been removed from the first cannula, the valve is adjusted to redirect the flow path such that the biomaterial can proceed through the first cannula and into the balloon.

The balloon is then filled with the flowable, uncured biomaterial and the biomaterial continues into the second cannula and exits therefrom until substantially all the air has been forced out of the device by the biomaterial. At this point. the exiting biomaterial can be inspected to undesirable characteristics, such as bubbling and the like. The filling and expansion of the balloon, and the curing of the biomaterial, are performed by controlling the fluid pressure of the biomaterial within the device throughout the procedure in accordance with a time period and pressure sufficient to maintain intervertebral distraction. Optionally, the disc can be distracted by ancillary devices as well, e.g., by the use of external or internal apparatuses such as bone screws distractor.

Optionally also, the disc can be pre-distracted, e.g., prior to delivery of the balloon itself (e.g., by mechanical means) and/or prior to delivery of the biomaterial (e.g., by delivery and recovery of a first fluid). Such pre-distraction can be performed, for instance, in conditions where it is desirable to diagnose the pain sources, determine the adequate distraction pressure and pre-stretch the tendons and ligaments prior to delivery of the balloon itself and/or biomaterial.

The flow path through the second cannula is controlled or restricted by way of the means for controlling the fluid pressure in such a manner that the balloon expands as a result of the fluid pressure. The balloon is filled and expanded at least sufficiently enough to substantially fill the balloon and interior cavity or chamber within the disc. The delivery time in combination with the fluid pressure during the distraction and curing process, and will vary according to the particular biomaterial used and its properties, e.g., viscosity and curing speed of the biomaterial.

The fluid pressure is increased and adjusted to an amount sufficient to distract the intervertebral disc space, thereby providing or restoring the anatomical geometry of the patient to the patient's needs. Typically, the pressure applied will range from about 0.2 mPA to about 1.5 mPA, or approximately 30 to 220 psi, and will vary according to the particular biomaterial, patient's condition, and integrity of the annulus. When the fluid pressure necessary to achieve this effect is reached, it is monitored and maintained through the curing stage to produce a prosthesis having the desired properties and dimensions (e.g., disc height and width).

Removing unnecessary portions or components of the system from the surgical site, e.g., severing and removing portions of the device extending beyond the disc site or annulus.

Once the curing of the biomaterial is complete, the introducing cannula and/or working cannula (when percutaneous approach is used) are withdrawal from the patient's body. The catheter connected to the balloon can be severed using any instrument adapted for cutting polymeric materials in the form of a cannula or tube. Preferably, the catheter (s) are severed as close to the balloon is possible.

Various devices and techniques can be used to repair the excised portion of the annulus following the procedure. For example, a tissue repair device can be used as described in applicant's own PCT Patent Application Serial No. PCT/US99/11740, the entire disclosure of which is incorporated herein by reference.

In one preferred embodiment, the balloon component of the device is inserted through the annulus and into the intervertebral disc space in order to position the balloon inside the nuclear portion of the disc. The balloon is filled with a curable biomaterial until it expands to the desired size (determined by distraction pressure and/or other means), wherein the desired size is maintained while the biomaterial subsequently cures in situ to form the prosthesis having the desired geometry and dimensions to restore the function of the disc.

In an alternative preferred embodiment, the system provides a device and biomaterial for use in replace the entire disc, including both the nucleus and annulus. Such an embodiment can include, for instance, the use of existing or modified devices and components such as endplate portions in the form of superior and inferior rigid metal endplates adapted to effectively sandwich the balloon and polymer of this invention. Those skilled in the art, given the present description, will be able to determine the manner in which such endplates can be used. (See Bao et al., "The artificial disc—theory, design and materials", Biomaterials 17:1157–1167, 1996)

The rigid endplates are used to enhance the fixation between the disc prosthesis and the intervertebral bodies. The fixation can be achieved by using either one or a combination of the following several design features; 1). Spikes, pegs or teeth on the outer surfaces perpendicular to the endplate, such as those disclosed in U.S. Pat. Nos. 4,759,766, 5,071,437, and 5,314,477. 2). Porous outer surfaces for bony ingrowth, such as those disclosed in U.S. Pat. Nos. 5,071,437, 5,314,478. 3). Side wings adapted to be fixed to the intervertebral body with bone screws, such as those disclosed in U.S. Pat. Nos. 5,458,642, 5,624,296 and 6,006,130. In any such embodiment, it is typically the less rigid polymer soft core that provides the desired flexibility to the overall prosthesis. The sandwiched soft core can either be bonded to the endplates or left mobile. If left mobile, it typically takes a ball and socket format with the inner surface of the endplates to be concave and the polymer core having a biconvex shape. This ball and socket design allows easier rotational (in both flexion-extension direction and lateral bending direction) movement while still maximize the stability of the core to be stayed in place.

While adopting various aspects of these approaches, the system of the present invention provides several differences and advantages as well. Prior designs tend to share at least one shortcoming, namely, the difficulty encountered in the course of inserting the implant into the disc space due to the overall bulk of the implant, especially when spikes, pegs or teeth are used. The present invention overcomes this problem by forming the central soft core in situ, using a flowable, curing biomaterial. While endplates with one or a combination of these three fixation features still can be used with the current invention for a total disc replacement, those portions can be more easily inserted and positioned either initially without a core, or with core in the form of a collapsed balloon. The biomaterial can than be delivered in the similar manner as the nucleus implant under controlled pressure to achieve optimal distraction.

In one preferred embodiment, the superior and inferior endplates are made of a metal, such as titanium alloy or Co—Cr alloy or stainless steel, with plurality of spikes or pegs adapted to face the respective vertebral bodies, and optionally having porous outer surfaces adapted to permit the eventual ingrowth of bone. The endplates each have concave and smooth inner, facing, surfaces, and are adapted to be mated so as to provide a slot opening between them with a dimension slightly larger than the balloon catheter diameter, thereby permitting an empty, collapsed balloon to be inserted. In one embodiment, after placing the endplates in position (which in turn, is done after disc material is removed), the balloon is inserted into the plate space. The balloon is then filled with in situ curable biomaterial. Under controlled injection pressure, the plates are pushed outward until the full penetration of the spikes into the vertebral bodies.

In an alternative embodiment, the endplates (each with a concave inner surface) also each have a side wing which allows fixation with a bone screw is used (similar to the one in U.S. Pat. No. 6,001,130). A gasket or other suitable means can be used to constrain the in situ cured nucleus. The two endplates can have a wall with a height of about half of the disc space to prevent the nucleus core migration. The wall of the two plates can have the same diameter or different diameters so they can overlap one over the other to further reduce the bulkiness during insertion.

Optionally, a system of this invention can be used to replace the entire disc without the use of endplates or use only one endplate. If no endplate is used, for instance, one or multiple anchors can be made on the intervertebral bodies. When polymer is injected, it will fill the anchors and create an interlock between the implant and intervertebral bodies. A suitable anchor can also be created by surgically shaving the superior and inferior surfaces to a suitable (preferably concave) shape, in order to effectively create mobile ball and socket interface after the polymer injection. Alternatively, an endplate can be used as an anchor on one surface, typically on the inferior surface, since the natural superior surface is more concave than the inferior surface.

Figure 11:
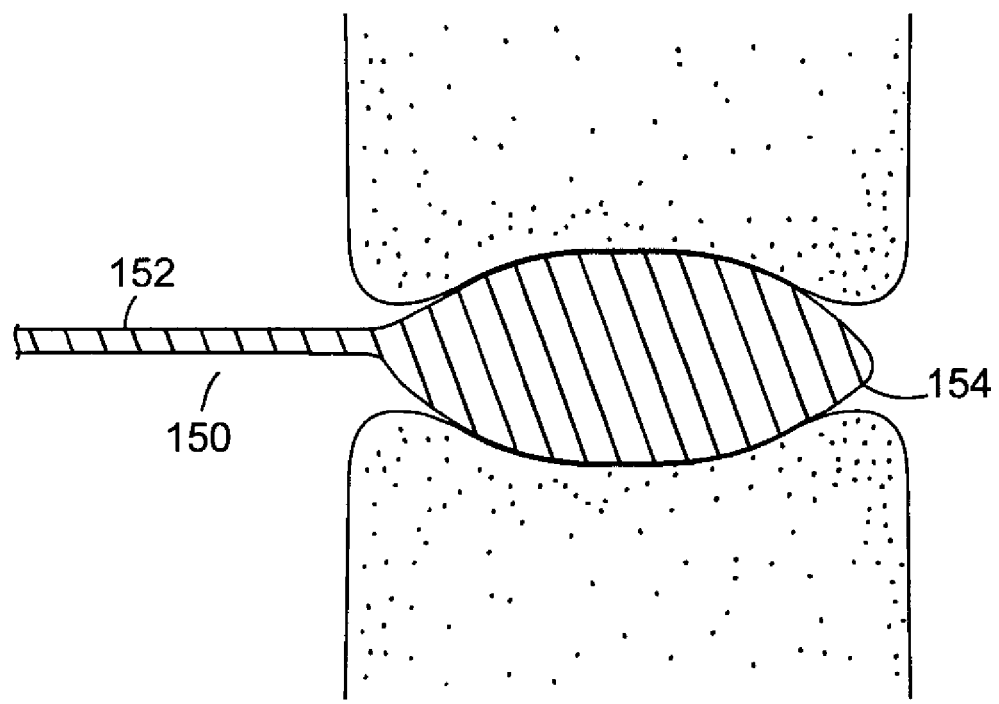
FIG. 11 shows a side view of an in situ curable disc implant between vertebrae.
Figure 12:
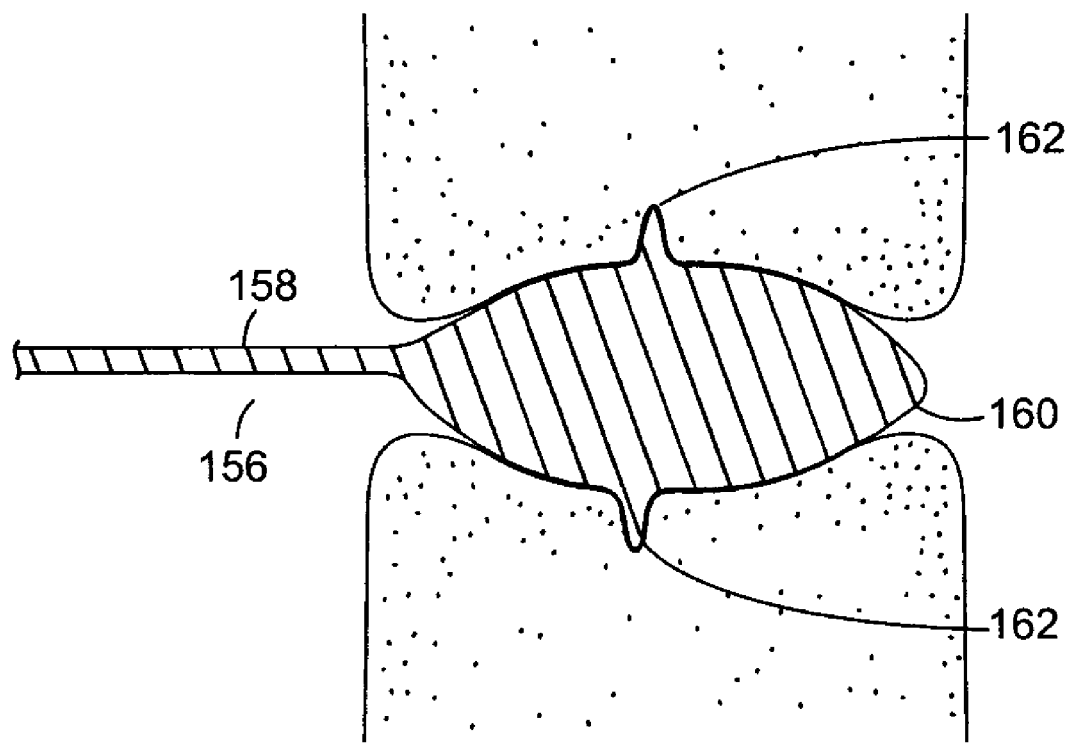
FIG. 12 shows a side view of disc implant between vertebrae with anchor points on the vertebral bodies.
Figure 13:
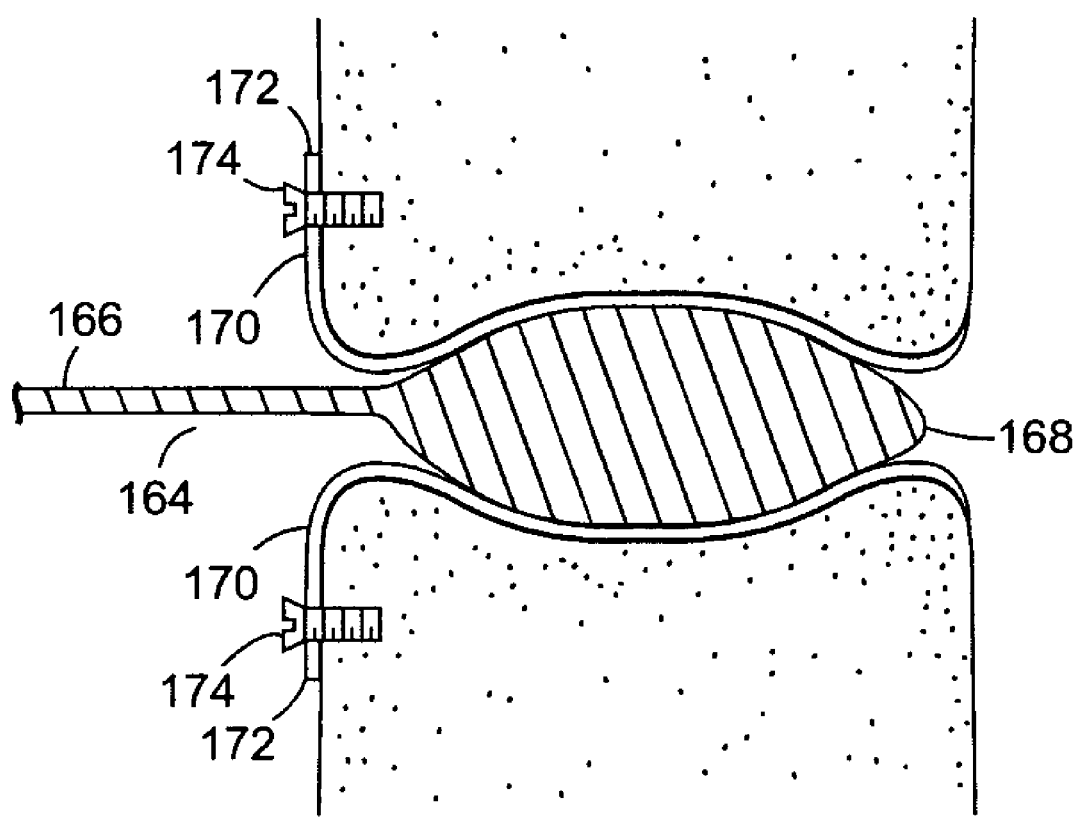
FIG. 13 shows a side view of a disc implant between endplates which have been fixed to the vertebral bodies using bone screws.
Figure 14:
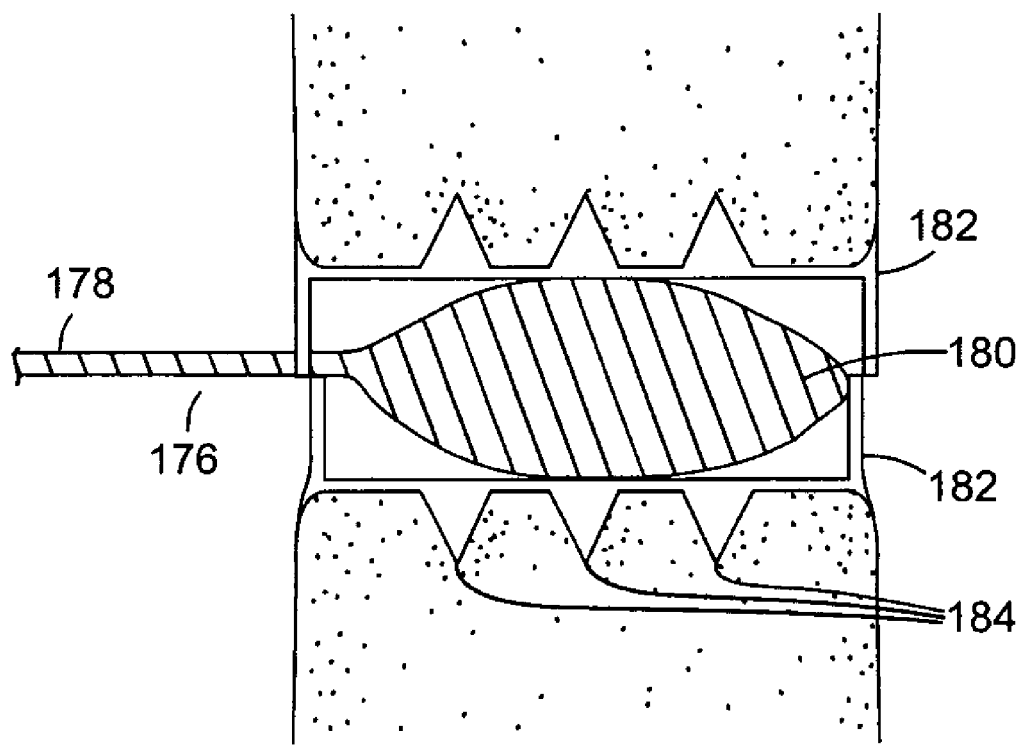
FIG. 14 shows a side view of a disc implant between endplates which have been fixed to the vertebral bodies using spikes on the outer surface of the endplates.

Figures of the systems of the invention mentioned above can be seen in FIGS. 11–14. FIG. 11 shows the balloon segment of the prosthesis in between the superior and inferior vertebral bodies without the use of endplates. FIG. 12 shows a system using anchor points which have been formed on the vertebral bodies. FIG. 13 shows the use of two metal endplates which have sidewings for fixation to the superior and inferior vertebral bodies using bone screws. The endplates have a smooth concave inner surface. FIG. 14 illustrates the use of endplates that have spikes on the outer surface which are pushed into the bone of the vertebral bodies. This system has a ring which is about one half the height of the disc prosthesis. The rings on the inferior and superior endplates have slightly different diameters respectively such that the rings overlap each other.

Also included in the invention is a prosthesis formed in situ using the device, system and method of the invention. In one embodiment, the prosthesis is provided within the annulus and in apposition to the endplates of a disc. In an alternative embodiment, the prosthesis is provided in a manner that substantially replaces the natural annulus, and optionally includes one or more prosthetic endplate components in apposition to natural bone.

EXAMPLES

Preparative Example 1

Formulation having 45% Hard Segment Content Prepared from 4,4'MDI, PTMO1000, 1,4BDO, TMP with NCO/OH=1

A formulation was prepared and designed to be used with the commercially available double-compartment cartridges with volume ratio between the compartments equal to 1, 2, 4, 10. It is intended to use this material in the temperature range between 30 and 40 C.

Prepolymer or quasi-prepolymers (Part A) were prepared having the following ingredients:

|  | Neq. | Total Weight g. | Total Weight % | A:B (Volume Ratio) | | | | |
|---|---|---|---|---|---|---|---|---|
|  |  |  |  | 0.5 % (Per Part A.) | 1.0 % (Per Part A.) | 2.0 % (Per Part A.) | 4.0 % (Per Part A.) | 10.0 % (Per Part A.) |
| MDI | 2.0 | 250.3 | 36.7 | 97.8 | 69.1 | 53.5 | 45.3 | 40.2 |
| PTMO1000 | 0.8 | 375.8 | 55.1 | 2.2 | 30.9 | 46.5 | 54.7 | 59.8 |
| 1,4BDO | 1.2 | 54.6 | 8.0 | 0.0 | 0.0 | 0.0 | 0.0 | 0.0 |
| TMP | 0.0 | 0.9 | 0.1 | 0.0 | 0.0 | 0.0 | 0.0 | 0.0 |
| HS |  |  |  | 44.9 | 44.9 | 44.9 | 44.9 | 44.9 |

-continued

|  | Neq. | Total Weight g. | Total Weight % | 0.5 % (Per Part A.) | A:B (Volume Ratio) 1.0 % (Per Part A.) | 2.0 % (Per Part A.) | 4.0 % (Per Part A.) | 10.0 % (Per Part A.) |
|---|---|---|---|---|---|---|---|---|
| NCO (%): |  |  |  | 32.6 | 20.5 | 13.9 | 10.5 | 8.4 |
| NCO/OH |  |  |  | 170.3 | 8.7 | 4.5 | 3.2 | 2.6 |
| Free MDI(% wt.) |  |  |  | 96.6 | 52.9 | 29.0 | 16.5 | 8.8 |
| urethanes |  |  |  | 0.3 | 3.7 | 5.6 | 6.6 | 7.2 |

Curative components (Part B) were prepared having the following ingredients:

|  | Neq. | Total Weight g. | Total Weight % | 0.5 % (Per Part B.) | A:B (Volume Ratio) 1.0 % (Per Part B.) | 2.0 % (Per Part B.) | 4.0 % (Per Part B.) | 10.0 % (Per Part B.) |
|---|---|---|---|---|---|---|---|---|
| MDI | 2.0 | 250.3 | 36.7 | 0.0 | 0.0 | 0.0 | 0.0 | 0.0 |
| PTMO1000 | 0.8 | 375.8 | 55.1 | 87.0 | 82.6 | 74.0 | 56.9 | 6.2 |
| 1,4BDO | 1.2 | 54.6 | 8.0 | 12.8 | 17.1 | 25.6 | 42.4 | 92.2 |
| TMP | 0.0 | 0.9 | 0.1 | 0.2 | 0.3 | 0.4 | 0.7 | 1.5 |

Preparative Example 2

Formulation with Hydrophobic Additive

A formulation having a hard segment (HS) ratio of 39.5% and A:B volume balance of 2 was prepared in the following manner:

| Reagent: | Neq. | Total Weight | Total Weight % | Weight A g | Weight B g | Weight A % | Weight B % |
|---|---|---|---|---|---|---|---|
| 4,4MDI | 2.0 | 250.3 | 33.3 | 250.3 | 0.0 | 48.8 | 0.0 |
| poly BD resin R20LM | 0.1 | 66.2 | 8.8 | 66.2 | 0.0 | 12.9 | 0.0 |
| PTMO1000 | 0.8 | 385.5 | 51.3 | 196.3 | 189.2 | 38.3 | 79.4 |
| 1,4butanediol | 1.1 | 49.2 | 6.5 | 0.0 | 49.2 | 0.0 | 20.6 |
| Cotin222 |  | 0.2 | 0.030 |  | 0.225 |  | 0.095 |
| Total |  | 751.4 | 100.0 | 512.8 | 238.4 | 100.0 | 100.0 |
| HS % |  |  |  | 39.9 |  |  |  |
| NCO (%) (part A): |  |  |  | 12.1 |  |  |  |
| NCO/OH (Part A) |  |  |  | 3.8 |  |  |  |
| CE % |  |  |  | 20.6 |  |  |  |
| MDI |  |  |  | 22.7 |  |  |  |
| Urethanes |  |  |  | 6.0 |  |  |  |

Preparative Example 3

A formulation was prepared in the following manner having a hard segement ratio of 43% and an A:B volume balance of 2.

| Reagent: | Neq. | Total Weight | Total Weight % | Weight A G | Weight B g | Weight A % | Weight B % |
|---|---|---|---|---|---|---|---|
| 4,4MDI | 2.0 | 250.3 | 34.8 | 250.3 | 0.0 | 50.7 | 0.0 |
| PTMO2000 | 0.2 | 150.0 | 20.9 | 150.0 | 0.0 | 30.4 | 0.0 |
| PTMO1000 | 0.5 | 258.6 | 36.0 | 93.0 | 165.6 | 18.9 | 73.6 |
| 1,4butanediol | 1.3 | 58.6 | 8.2 | 0.0 | 58.6 | 0.0 | 26.0 |
| TMP | 0.0 | 0.9 | 0.1 | 0.0 | 0.9 | 0.0 | 0.4 |
| UL-22 | | 0.2 | 0.030 | | 0.2 | | 0.1 |
| Total | | 718.6 | 100.0 | 493.3 | 225.1 | 100.0 | 100.0 |
| | HS | | | | 43.1 | | |
| | NCO (%): | | | | 14.1 | | |
| | NCO/OH | | | | 5.9 | | |
| | TMP X-links | | | | 9.26E−06 | | |
| | CE % | | | | 26.4 | | |
| | MDI | | | | 33.0 | | |
| | Urethanes | | | | 4.1 | | |

Preparative Example 4

A formulation was prepared based on MDI-PTMO2000 and 1,4BDO-TMP, having an A:B volume ratio of 10 and using 1,4 BDO-TMP mixture as a curative.

| Reagent: | Neq. | Total Weight g. | Total Weight % | Weight A g | Weight B g | Weight A % | Weight B % |
|---|---|---|---|---|---|---|---|
| 4,4MDI | 2.0 | 250.3 | 31.6 | 250.3 | 0.0 | 34.6 | 0.0 |
| PTMO2000 | 0.5 | 472.3 | 59.7 | 472.3 | 0.0 | 65.4 | 0.0 |
| 1,4butanediol | 1.5 | 67.8 | 8.6 | 0.0 | 67.8 | 0.0 | 98.4 |
| TMP | 0.0 | 1.1 | 0.1 | 0.0 | 1.1 | 0.0 | 1.6 |
| UL-22 | | 0.2 | 0.03 | | 0.2 | | 0.3 |
| Total | | 791.7 | 100.0 | 722.6 | 68.9 | 100.0 | 100.0 |
| | HS | | | | 40.3 | | |
| | NCO (%): | | | | 8.9 | | |
| | NCO/OH | | | | 4.2 | | |
| | TMP X-links | | | | 1.1E−05 | | |
| | CE % | | | | 100.0 | | |
| | MDI | | | | 17.9 | | |
| | Urethanes | | | | 3.9 | | |

Preparative Example 5

A formulation was prepared in the following manner having pure isocyanate as a Part A: A:B volume ratio of 0.5.

| Reagent: | Neq. | Total Weight | Total Weight % | Weight A g | Weight B g | Weight A % | Weight B % |
|---|---|---|---|---|---|---|---|
| Mondur ML | 2.0 | 250.3 | 37.7 | 250.3 | 0.0 | 100.0 | 0.0 |
| PTMO2000 | 0.7 | 356.9 | 53.7 | 0.0 | 356.9 | 0.0 | 86.2 |
| 1,4butanediol | 1.2 | 56.3 | 8.5 | 0.0 | 56.3 | 0.0 | 13.6 |
| TMP | 0.0 | 0.9 | 0.1 | 0.0 | 0.9 | 0.0 | 0.2 |
| UL-22 | | 0.2 | 0.03 | | 0.2 | | 0.048 |
| Total | | 664.5 | 100.0 | 250.3 | 414.1 | 100.0 | 100.0 |
| | HS | | | | 46.3 | | |
| | NCO (%): | | | | 33.6 | | |
| | NCO/OH | | | | | | |

-continued

| | |
|---|---|
| TMP X-links | 1.0E−05 |
| CE % | 13.8 |
| MDI | 100.0 |
| Urethanes | 0.0 |

Example 1

Nucleus Implant

An illustration of the surgical use of one embodiment of the intervertebral prosthesis system of the invention is as follows 1) A discectomy is performed by surgically accessing the disc through the annulus (annulotomy) and removing the nuclear portion of the disc.
2) The proximal (patient end) portion of a device of this invention is inserted into the surgical site and intervertebral space. The proximal tip, containing a deflated, compacted balloon encased within a surgical delivery introducing cannula, is inserted through the annular incision. The balloon is then deployed from the introducing cannula by pushing the proximal end of the biomaterial delivery portion in a longitudinal direction through the surgical cannula in the direction of the disc to the extent necessary to expel the balloon only into the nuclear chamber.
3) Optionally, if pre-distraction of the intervertebral disc is needed when the patient has pre-exist disc height loss, it can be accomplished using any suitable intervertebral distraction means, including both external or internal means. Internal distraction can be accomplished by using an apparatus similar to that of the invention, e.g., by first delivering a suitable solution (e.g., saline or contrast solution) into the balloon in order to exert a force sufficient to "distract" the intervertebral joint to the desired extent. After the distraction, the solution can be removed from the balloon by applying vacuum. It is optional either to use the same balloon for hosting the injectable biomaterial or to replace the distraction balloon with a new balloon.
4) The proximal (entry) end of the static mixer device together with the purge system is then attached to the distal end (exit port) of the biomaterial source.
5) The components of the fluid pressure monitoring system are assembled. In one embodiment, one end of the fluid transmission conduit is attached to the pressure gauge and the other end is attached to the adaptor (juncture and valve assembly) which in turn connects to the apparatus between the exit end of the biomaterial mixing path and the distal portion of the static mixer device and purge system assembly. Each end of the transmission fluid conduit contains a valve—one, for transmission fluid inlet and one for transmission fluid outlet. The inlet and outlet valves are opened and pressure transmission fluid is delivered into the conduit through the inlet until the conduit is completely filled and the excess flows out the outlet end. The conduit is then attached to the pressure gauge and calibrated as needed.
6) The proximal end of the biomaterial delivery portion of the apparatus is then attached to the distal end of the static mixer together with the associated biomaterial source/purge system/pressure monitoring system assembly.
7) The distal end of the biomaterial outlet conduit of the biomaterial delivery portion of the apparatus is then attached to the vacuum source. Attachment can be accomplished by a variety of suitable means, including attachment through a controllable valve in order to manipulate the amount of negative pressure exerted through the conduit during the air removal and biomaterial delivery phases of the procedure.
8) The vacuum source is then activated with a closed biomaterial delivery portion by way of a (proximally located valve in the closed position) and air is removed from the inside of the balloon to create a negative pressure environment.
9) The fluid pressure transmission system is activated (opened) and the biomaterial components are then forced by positive pressure out of the container and through the static mixing device, and the initially inadequately mixed portion of the mixed biomaterial is shunted through the purge system by directing the purge valve accordingly.
10) Once the initial portion of the biomaterial has been shunted, the valve is redirected to permit the biomaterial to continue onward through the flow path and into the biomaterial delivery portion of the device through the first lumen which channels the biomaterial into the interior of the balloon.
11) The balloon is filled and the excess biomaterial and air exits through the second lumen running through the biomaterial outlet conduit toward the negative pressure source. The negative pressure is controlled in conjunction with the positive pressure of the biomaterial delivery to obtain the desired balloon size and internal pressure for the particular patient's needs. The fluid pressure in the entire apparatus is continually monitored and manipulated during the entire filling phase of the procedure.
12) When the desired pressure and amount of biomaterial have been accomplished, the parameters are maintained during the curing phase of the biomaterial.
13) The apparatus is detached at the juncture between the biomaterial delivery portion and the remainder of the, apparatus, and the surgical cannula is retracted from the site.
14) The shaft of the balloon is severed using any suitable technique or instrument adapted to accomplish such, and the biomaterial delivery portion of the apparatus is then removed from the site, thereby leaving the filled balloon containing the cured biomaterial in situ to function as an intervertebral disc prosthesis. The patient is sutured and closed and permitted to recover from the surgery. The parameters of the surgery will vary according to a number of factors, including but not limited to biomaterial flow rate, the desired properties and dimensions of the ultimate prosthesis, biomaterial curing time, biomaterial fluid pressure, distraction pressure, distraction time, biomaterial properties (such as flowability, temperature, and the like specific to the particular formulation used), and the cavity site spatial parameters.

Example 2

Total Disc Implant

Various surgical approaches and techniques can be used to implant the disc prosthesis. If rigid endplates are used, it almost requires an open anterior or retroperitoneal approach. The main advantage of these two approaches is allowing surgeon full assess to the disc space for a complete disc removal so a big endplate can be used to cover the entire disc space.

1) The first step involves the removal of degenerative disc material using any existing surgical techniques and approaches. If possible, it can be desirable to leave the outer layers of the annulus and the ligaments.
2) If artificial endplates are used, insert the endplates into the disc space and position the plates in the center of the disc space. If the endplates have side wing(s), fix the side wing(s) with bone screws.
3) Optionally, predistract the disc in the manner described herein (e.g., by the use of an initial solution).
4) The proximal end of the static mixer device together with the purge system is then attached to the distal end (exit port) of the biomaterial source.
5) The fluid pressure monitoring system is assembled separately. In one embodiment, one end of the fluid transmission conduit is attached to the pressure gauge and the other end is attached to the juncture and valve assembly which in turn connects to the apparatus between the proximal portion of the biomaterial delivery portion of the apparatus and the distal portion of the static mixer device and purge system assembly. Each end of the transmission fluid conduit contains a valve—one, for transmission fluid inlet and one for transmission fluid outlet. The inlet and outlet valves are opened and pressure transmission fluid is delivered into the conduit through the inlet until the conduit is completely filled and the excess flows out the outlet end. The conduit is then attached to the pressure gauge and calibrated as needed.
6) The proximal end of the biomaterial delivery portion of the apparatus is then attached to the distal end of the static mixer together with the associated biomaterial source/purge system/pressure monitoring system assembly.
7) The distal end of the biomaterial outlet conduit of the biomaterial delivery portion of the apparatus is then attached to the vacuum source. Attachment can be accomplished by a variety of suitable means, including attachment through a controllable valve in order to manipulate the amount of negative pressure exerted through the conduit during the air removal and biomaterial delivery phases of the procedure.
8) The vacuum source is then activated with a closed biomaterial delivery portion by way of a (proximally located valve in the closed position) and air is removed from the inside of the balloon to create a negative pressure environment.
9) The fluid pressure transmission system is activated (opened) and the biomaterial components are then forced by positive pressure out of the container and through the static mixing device, and the initially inadequately mixed portion of the mixed biomaterial is shunted through the purge system by directing the purge valve accordingly.
10) Once the initial portion of the biomaterial has been shunted, the valve is redirected to permit the biomaterial to continue onward through the flow path and into the biomaterial delivery portion of the device through the first lumen which channels the biomaterial into the interior of the balloon.
11) The balloon is filled and the excess biomaterial and air exits through the second lumen running through the biomaterial outlet conduit toward the negative pressure source. The negative pressure is controlled in conjunction with the positive pressure of the biomaterial delivery to obtain the desired balloon size and internal pressure for the particular patient's needs. The fluid pressure in the entire apparatus is continually monitored and manipulated during the entire filling phase of the procedure.
12) When the desired pressure and amount of biomaterial have been accomplished, the parameters are maintained during the curing phase of the biomaterial.
13) The apparatus is detached at the juncture between the biomaterial delivery portion and the remainder of the apparatus, and the surgical cannula is retracted from the site.
14) The shaft of the balloon is severed using any suitable technique or instrument adapted to accomplish such, and the biomaterial delivery portion of the apparatus is then removed from the site, thereby leaving the filled balloon containing the cured biomaterial in situ to function as an intervertebral disc prosthesis. The patient is sutured and closed and permitted to recover from the surgery.

The parameters of the surgery will vary according to a number of factors, including but not limited to biomaterial flow rate, the desired properties and dimensions of the ultimate prosthesis, biomaterial curing time, biomaterial fluid pressure, distraction pressure, distraction time, biomaterial properties (such as flowability, temperature, and the like specific to the particular formulation used), and the cavity site spatial parameters.

What is claimed is:

1. A method for repairing or resurfacing the site of an injured or diseased articulating joint, the method comprising the steps of:
   providing a curable biomaterial; and
   performing the surgical steps of;
   (a) accessing and preparing the joint site for receipt of the biomaterial;
   (b) delivering a quantity of the curable biomaterial to the prepared joint site;
   (c) curing the delivered biomaterial in such a manner that the cured biomaterial is permanently retained in apposition to the prepared site; and contouring the cured, retained biomaterial to achieve a desired conformation approximating that of the natural joint, wherein steps (a) through (c) comprise an intervertebral disc replacement using minimally invasive surgical means.

2. The method according to claim 1 wherein the minimally invasive surgical means are arthroscopic means.

3. The method according to claim 1 wherein the delivery step is performed under arthroscopic visualization using a cannula suitably dimensioned to deliver the curable biomaterial.

4. The method according to claim 1 comprising the further step of coating or modifying the surface of the contoured material with a permanent interface material in order to improve the biocompatability or coefficient of friction of the cured biomaterial, wherein the coating or modifying step is also performed using minimally invasive surgical means.

5. The method according to claim 1 wherein the biomaterial comprises a curable polyurethane polymer.

6. The method according to claim 1 wherein the delivery step is performed using an arthroscopic cannula.

7. The method according to claim 1 wherein the intervertebral disc comprises a mold for retaining the curable biomaterial.

8. A method for repairing a damaged or diseased intervertebral disc, the method comprising the steps of:
using minimally invasive techniques to remove damaged or diseased nucleus from the disc;
providing a mold apparatus comprising a balloon adapted to contain a biomaterial and a delivery cannula adapted to flowably connect a biomaterial source to the balloon;
positioning the balloon in the intervertebral disc space using minimally invasive techniques;
providing a biomaterial source comprising a flowable biomaterial;
mixing the flowable biomaterial;
purging a portion of the flowable biomaterial prior to delivery to the intervertebral disc space;
delivering the flowable biomaterial into the balloon using minimally invasive techniques to provide a distraction pressure to the intervertebral disc space;
allowing the delivered biomaterial to cure a sufficient amount to permit the cannula to be removed and to provide a permanent replacement for the nucleus.

9. The method of claim 8 wherein the biomaterial comprises a polyurethane system.

10. The method of claim 8 wherein the balloon when inflated fills less than the entire volume of the intervertebral disc space.

11. The method of claim 8 comprising locating biomaterial in the intervertebral disc space outside of the balloon.

12. The method of claim 11 wherein the biomaterial located in the intervertebral disc space outside of the balloon is different from the biomaterial located in the balloon.

13. The method of claim 11 wherein the biomaterial located in the balloon is more flexible than the biomaterial located in the intervertebral disc space outside of the balloon.

14. The method of claim 11 wherein the biomaterial located outside of the balloon is in-situ curable.

15. The method of claim 8 comprising purging a portion of the biomaterial prior to delivery to the balloon.

16. The method of claim 8 comprising purging a volume of biomaterial equal to about 1 to about 4 times a volume of a mixing element prior to delivery of the biomaterial to the balloon.

17. The method of claim 8 wherein the delivery of biomaterial is done at a substantially constant flow rate.

18. The method of claim 8 wherein the delivery of biomaterial is done at a substantially continuous flow rate.

19. A method for repairing a damaged or diseased intervertebral disc, the method comprising the steps of:
using minimally invasive techniques to remove damaged or diseased nucleus from the disc; providing a mold apparatus comprising a balloon adapted to contain a biomaterial and a delivery cannula adapted to flowably connect a biomaterial source to the balloon;
positioning the balloon in the intervertebral disc space using minimally invasive techniques;
providing a biomaterial source comprising a flowable biomaterial;
mixing the flowable biomaterial;
withdrawing air from the balloon located in the intervertebral disc space;
delivering the flowable biomaterial into the balloon using minimally invasive techniques to provide a distraction pressure to the intervertebral disc space; and
allowing the delivered biomaterial to cure a sufficient amount to permit the cannula to be removed and to provide a permanent replacement for the nucleus.

20. The method of claim 19 wherein the biomaterial comprises a polyurethane system.

21. The method of claim 19 wherein the balloon when inflated fills less than the entire volume of the intervertebral disc space.

22. The method of claim 19 comprising locating biomaterial in the intervertebral disc space outside of the balloon.

23. The method of claim 22 wherein the biomaterial located in the intervertebral disc space outside of the balloon is different from the biomaterial located in the balloon.

24. The method of claim 22 wherein the biomaterial located in the balloon is more flexible than the biomaterial located in the intervertebral disc space outside of the balloon.

25. The method of claim 22 wherein the biomaterial located in the annular shell is in-situ curable.

26. The method of claim 19 comprising applying herein mechanical distraction in combination with the pressurized injection of flowable biomaterial to apply a distraction force to the intervertebral disc space.

27. The method of claim 19 comprising purging a portion of the biomaterial prior to delivery to the balloon.

28. The method of claim 19 comprising purging a volume of biomaterial equal to about 1 to about 4 times a volume of a mixing element prior to delivery of the biomaterial to the balloon.

29. The method of claim 19 wherein the delivery of biomaterial is done at a substantially constant flow rate.

30. The method of claim 19 wherein the delivery of biomaterial is done at a substantially continuous flow rate.

31. A method for repairing a damaged or diseased intervertebral disc, the method comprising the steps of:
using minimally invasive techniques to remove damaged or diseased nucleus from the disc;
providing a mold apparatus comprising a balloon adapted to contain a biomaterial and a delivery cannula adapted to flowably connect a biomaterial source to the balloon;
positioning the balloon in the intervertebral disc space using minimally invasive techniques;
providing a biomaterial source comprising a flowable biomaterial;
mixing the flowable biomaterial;
delivering the flowable biomaterial into the balloon using minimally invasive techniques to provide a distraction pressure to the intervertebral disc space; and
allowing the delivered biomaterial to cure a sufficient amount to permit the cannula to be removed and to provide a permanent replacement for the nucleus, wherein the cured biomaterial provides a heterogeneous implant having a plurality of regions with a more rigid outer region and a more flexible inner region.

32. The method of claim 31 wherein the injection of pressurized biomaterial is sufficient to distract the intervertebral disc space from constricted dimensions of on the order of 3 mm to 4 mm to dimensions of on the order of 8 mm to 12 mm.

33. The method of claim 31 wherein the biomaterial comprises a polyurethane system.

34. The method of claim 31 wherein the balloon when inflated fills less than the entire volume of the intervertebral disc space.

35. The method of claim 31 comprising locating biomaterial in the intervertebral disc space outside of the balloon.

36. The method of claim 35 wherein the biomaterial located in the intervertebral disc space outside of the balloon is different from the biomaterial located in the balloon.

37. The method of claim 35 wherein the biomaterial located in the balloon is more flexible than the biomaterial located in the intervertebral disc space outside of the balloon.

38. The method of claim 31 wherein the biomaterial located in the annular shell is in-situ curable.

39. The method of claim 31 comprising applying mechanical distraction in combination with the pressurized injection of flowable biomaterial to apply a distraction force to the intervertebral disc space.

40. The method of claim 31 comprising purging a portion of the biomaterial prior to delivery to the balloon.

41. The method of claim 31 comprising purging a volume of biomaterial equal to about 1 to about 4 times a volume of a mixing element prior to delivery of the biomaterial to the balloon.

42. The method of claim 31 wherein the delivery of biomaterial is done at a substantially constant flow rate.

43. The method of claim 31 wherein the delivery of biomaterial is done at a substantially continuous flow rate.

44. A method for repairing a damaged or diseased intervertebral disc, the method comprising the steps of:

using minimally invasive techniques to remove damaged or diseased nucleus from the disc;

providing a mold apparatus comprising a balloon adapted to contain a biomaterial and a delivery cannula adapted to flowably connect a biomaterial source to the balloon;

positioning the balloon in the intervertebral disc space using minimally invasive techniques;

providing a biomaterial source comprising a flowable biomaterial;

mixing the flowable biomaterial;

purging a portion of the biomaterial prior to delivery to the balloon;

delivering the flowable biomaterial into the balloon using minimally invasive techniques; and allowing the delivered biomaterial to cure a sufficient amount to permit the cannula to be removed and to provide a permanent replacement for the nucleus.

45. The method of claim 44 wherein the step of purging comprises purging a volume of biomaterial equal to about 1 to about 4 times a volume of a mixing element prior to delivery of the biomaterial to the balloon.

46. The method of claim 44 wherein the delivery of biomaterial is done at a substantially constant flow rate.

47. The method of claim 44 wherein the delivery of biomaterial is done at a substantially continuous flow rate.

48. A method for repairing a damaged or diseased intervertebral disc, the method comprising the steps of:

using minimally invasive techniques to remove damaged or diseased nucleus from the disc;

providing a mold apparatus comprising a balloon adapted to contain a biomaterial and a delivery cannula adapted to flowably connect a biomaterial source to the balloon;

positioning the balloon in the intervertebral disc space using minimally invasive techniques;

providing a biomaterial source comprising a flowable biomaterial;

mixing the flowable biomaterial;

delivering the flowable biomaterial into the balloon located in the intervertebral disc space while applying a vacuum to the balloon using minimally invasive techniques;

terminating the flow of biomaterial in response to an endpoint monitor adapted to provide an indication of an endpoint for biomaterial delivery; and allowing the delivered biomaterial to cure a sufficient amount to permit the cannula to be removed and to provide a permanent replacement for the nucleus.

49. The method of claim 48 wherein the endpoint for delivery of biomaterial is determined by delivery pressure of the biomaterial.

50. The method of claim 48 wherein the endpoint for delivery of biomaterial is determined by volume of biomaterial delivered.

51. The method of claim 48 wherein the endpoint for delivery of biomaterial is determined by the amount of distraction of the intervertebral disc.

52. A method for repairing or resurfacing the site of an injured or diseased articulating joint, the method comprising the steps of:

providing a curable biomaterial; and performing the surgical steps of;

(a) accessing and preparing the joint site for receipt of the biomaterial;

(b) purging a portion of the biomaterial prior to delivery into the prepared joint site;

(c) delivering a quantity of the curable biomaterial to the prepared joint site;

(d) curing the delivered biomaterial in such a manner that the cured biomaterial is permanently retained in apposition to the prepared site; and contouring the retained biomaterial to achieve a desired conformation approximating that of the natural joint, wherein steps (a) through (d) comprise an intervertebral disc replacement using minimally invasive surgical means.

53. The method according to claim 52 wherein the biomaterial comprises a curable polyurethane polymer.

54. The method according to claim 52 wherein the delivery step is performed using an arthroscopic cannula.

55. The method according to claim 52 wherein the intervertebral disc site comprises a mold for retaining the curable biomaterial.

56. The method according to claim 19 wherein air is withdrawn from the balloon at the same time the flowable biomaterial is delivered into the balloon.

57. The method according to claim 7 comprising providing a mold with elastic properties and non-elastic properties at different regions.

58. The method according to claim 7 wherein at least one lateral wall of the mold comprises a compliance value higher than a delivery pressure of the biomaterial.

59. The method according to claim 7 wherein the mold provides a distraction force in essentially a vertical direction without exerting a high expansion force on a surrounding annulus.

60. The method according to claim 7 comprising incorporating a reinforcing material in at least a portion of the mold.

61. The method according to claim 8 comprising providing a mold with elastic properties and non-elastic properties at different regions.

62. The method according to claim 8 wherein at least one lateral wall of the balloon comprises a compliance value higher than a delivery pressure of the biomaterial.

63. The method according to claim 8 wherein the balloon provides a distraction force in essentially a vertical direction without exerting a high expansion force on a surrounding annulus.

64. The method according to claim 8 comprising incorporating a reinforcing material in at least a portion of the balloon.

65. The method according to claim 19 comprising providing a mold with elastic properties and non-elastic properties at different regions.

66. The method according to claim 19 wherein at least one lateral wall of the balloon comprises a compliance value higher than a delivery pressure of the biomaterial.

67. The method according to claim 19 wherein the balloon provides a distraction force in essentially a vertical direction without exerting a high expansion force on a surrounding annulus.

68. The method according to claim 19 comprising incorporating a reinforcing material in at least a portion of the balloon.

69. The method according to claim 44 comprising providing a mold with elastic properties and non-elastic properties at different regions.

70. The method according to claim 44 wherein at least one lateral wall of the balloon comprises a compliance value higher than a delivery pressure of the biomaterial.

71. The method according to claim 44 wherein the balloon provides a distraction force in essentially a vertical direction without exerting a high expansion force on a surrounding annulus.

72. The method according to claim 44 comprising incorporating a reinforcing material in at least a portion of the balloon.

* * * * *

UNITED STATES PATENT AND TRADEMARK OFFICE
CERTIFICATE OF CORRECTION

PATENT NO.       : 7,077,865 B2
APPLICATION NO.  : 10/365842
DATED            : July 18, 2006
INVENTOR(S)      : Qi-Bin Bao et al.

It is certified that error appears in the above-identified patent and that said Letters Patent is hereby corrected as shown below:

On the Title page of the patent, item (60) "Related U.S. Application Data"

Delete the following:

"Continuation-in-part of application No. 09/649,491, filed on Aug. 28, 2000, now abandoned, which is a continuation-in-part of application No. 08/993,468, filed on Dec. 18, 1997, now Pat. No. 6,306,177, which is a continuation of application No. PCT/US97/20874, filed on Nov. 14, 1997, which is a continuation-in-part of application No. 08/903,455, filed on Jul. 30, 1997, now abandoned, and a continuation-in-part of application No. 08/749,429, filed on Nov. 15, 1996, now abandoned, which is a continuation-in-part of application No. 08/742,444, filed on Nov, 2, 1996, now Pat. No. 5,795,353, which is a continuation-in-part of application No. 08/590,293, filed on Jan. 23, 1996, now Pat. No. 5,888,220, which is a continuation of application No. 08/474,113, filed on Jun. 7, 1995, now abandoned, which is a division of application No. 08/239,248, filed on May 6, 1994, now Pat. No. 5,556,429.
Provisional application No. 60/056,624, filed on Aug. 20, 1997."

and replace it with the following:
-- Continuation-in-part of application No. 09/649,491, filed on Aug. 28, 2000, now abandoned, which is a continuation-in-part of application No. 08/993,468, filed on Dec. 18, 1997, now Pat. No. 6,306,177, which is a continuation of application No. PCT/US97/20874, filed on Nov. 14, 1997; and said application No. 08/993,468 claims priority to application No. 60/056,624, filed on Aug. 20, 1997; and as a continuation-in-part of patent application No. 08/749,429, filed Nov. 15, 1996, now abandoned, which is a continuation-in-part of application No. 08/742,444, filed on Nov. 2, 1996, now Pat. No. 5,795,353, which is a continuation of application No. 08/474,113, filed on Jun.7, 1995,

UNITED STATES PATENT AND TRADEMARK OFFICE
CERTIFICATE OF CORRECTION

PATENT NO. : 7,077,865 B2
APPLICATION NO. : 10/365842
DATED : July 18, 2006
INVENTOR(S) : Qi-Bin Bao et al.

It is certified that error appears in the above-identified patent and that said Letters Patent is hereby corrected as shown below:

now abandoned, which is a divisional of application No. 08/239,248, filed on May 6, 1994, now Pat. No. 5,556,429; and said application No. 08/993,468 is a continuation-in-part of patent application No. 08/903,455, filed Jul. 30, 1997, now abandoned, which is a continuation-in-part of application No. 08/590,293, filed Jan. 23, 1996, now Pat. No. 5,888,220. --

Signed and Sealed this

Nineteenth Day of December, 2006

JON W. DUDAS
*Director of the United States Patent and Trademark Office*